(12) United States Patent
Kusters et al.

(10) Patent No.: US 7,514,547 B2
(45) Date of Patent: Apr. 7, 2009

(54) HELICOBACTER FELIS VACCINE

(75) Inventors: Johannes Gerardus Kusters, Bunnik (NL); Giovanni Cattoli, Padua (IT)

(73) Assignee: Intervet International B.V., Boxmeer (NL)

( * ) Notice: Subject to any disclaimer, the term of this patent is extended or adjusted under 35 U.S.C. 154(b) by 324 days.

(21) Appl. No.: 09/904,994

(22) Filed: Jul. 13, 2001

(65) Prior Publication Data

US 2004/0005325 A1    Jan. 8, 2004

(30) Foreign Application Priority Data

Jul. 17, 2000    (EP) .................................. 00202565

(51) Int. Cl.
*A61K 39/00* (2006.01)

(52) U.S. Cl. ...................... 536/23.7; 514/44; 435/69.1; 435/252.3

(58) Field of Classification Search ................ 536/23.1, 536/23.7; 514/44, 12; 435/6, 69.1; 503/350, 503/300; 424/150.1, 184.1, 193.1, 278.1, 424/283.1, 234.1
See application file for complete search history.

(56) References Cited

U.S. PATENT DOCUMENTS

| | | | | |
|---|---|---|---|---|
| 5,610,060 | A | * 3/1997 | Ward et al. ................ | 435/252.1 |
| 5,843,460 | A | * 12/1998 | Labigne et al. ........... | 424/234.1 |
| 5,985,631 | A | * 11/1999 | Soman et al. ................ | 435/184 |
| 6,039,959 | A | * 3/2000 | Burnie ..................... | 424/234.1 |
| 6,248,330 | B1 | * 6/2001 | Labigne et al. ........... | 424/192.1 |
| 6,258,359 | B1 | * 7/2001 | Labigne et al. ........... | 424/141.1 |
| 6,793,921 | B2 | * 9/2004 | Kodama et al. ........... | 424/157.1 |
| 2002/0146423 | A1 | * 10/2002 | Doidge et al. ............. | 424/184.1 |
| 2003/0007980 | A1 | * 1/2003 | Michetti et al. ........... | 424/190.1 |
| 2003/0158396 | A1 | * 8/2003 | Kleanthous et al. ....... | 536/23.1 |
| 2003/0180330 | A1 | * 9/2003 | Meyer et al. .............. | 424/234.1 |

FOREIGN PATENT DOCUMENTS

| | | | |
|---|---|---|---|
| JP | 090087297 | * | 3/1997 |
| WO | WO 94/26901 | | 11/1994 |

OTHER PUBLICATIONS

Swiss-Prot Accession No. P50043, *Mycobacterium tuberculosis* urease fragment polypeptide.*

Gootz, Thomas D et al, Infection and Immunity, vol. 62(3), pp. 793-798, May 1994, Immunological and molecular characterization of *Helicobacter felis* urease.*
Lee, Adrian et al, Infection and IMmunity, Nov. 1988, vol. 56(110, pp. 2843-2850, Isolation of a Sprial-Shaped bacterium from the cat stomach.*
Simpson, Kenneth W et al, Infection and Immunity, vol. 68(2), pp. 779-790, Feb. 2000, *Helicobacter felis* Infection is associated with Lymphoid Follicular Hyperplasia and Mild Gastritis but normal Gastric SEcretoty Function in cats.*
Permin et al, Vaccine, vol. 10, Suppl. 1, 2005, pp. 21-25.*
Bourinbaiar, AS et al, Current Pharmaceutical Design, 2006, vol. 12, pp. 2017-2030.*
Baird, M et al, Scandinavian Journal of Immunology, vol. 60, pp. 363-371.*
Lee, CK et al, Oral immunization with recombinant *Helicobacter pylori* urease induces secretory IgA antibodies and protects mice from challenge with *Helicobacter felis*. J. Infect. Dis, 1995, vol. 172, pp. 161-172.*
Gootz et al 1994, reference of record.*
Jalava, K et al, Applied and Environmental Microbiology, vol. 64(10), pp. 3998-4006, Oct. 1998, Isolation and Identification of *Helicobacter* spp. from Canine and Feline Gastric Mucosa.*
Myers, G. A. et al.: "Oral immunization with recombinant *Helicobacter pylori* urease confers long-lasting immunity against *Helicobacter felis* infection", Vaccine, GB, Butterworth Scientific. Guildford, vol. 17, No. 11-12, Mar. 1999, pp. 1394-1403; p. 1401; table 1.
Blanchard T. G. et al.: "Urease-Specific Monoclonal Antibodies Prevent *Helicobacter felis* Infection in Mice", Infection and Immunity, US, American Society for Microbiology. Washington, vol. 63, No. 4, Apr. 1, 1995, pp. 1394-1399; p. 1396, col. 2; figures 1-3, 6.

* cited by examiner

*Primary Examiner*—Mark Navarro
*Assistant Examiner*—Ginny Portner
(74) *Attorney, Agent, or Firm*—William M. Blackstone; Aaron L. Schwartz

(57) ABSTRACT

The present invention relates to novel *Helicobacter felis* urease subunit polypeptides and to nucleic acid sequences encoding these subunit polypeptides, to DNA fragments and recombinant DNA molecules comprising the nucleic acid sequences encoding these subunit polypeptides, to live recombinant carriers and to host cells comprising nucleic acid sequences encoding these subunit polypeptides. Also, the invention relates to the subunit polypeptides for use in vaccines and the use in the manufacturing thereof, to vaccines comprising said subunit polypeptides and to methods for the preparation of such vaccines. Furthermore, the invention relates to diagnostic methods for the detection of *Helicobacter felis* specific nucleic acid sequences, *Helicobacter felis* antigenic material and to antibodies against *Helicobacter felis*.

7 Claims, 8 Drawing Sheets

ALIGNED SEQUENCES

Reference molecule: ureXCS1    1 - 226    ( 226 aa)    Homology

| Sequence 2: | ureXkuka | 1 - 226 | ( 226 aa) | 100% |
|---|---|---|---|---|
| Sequence 3: | ureXDS4 | 1 - 226 | ( 226 aa) | 99% |
| Sequence 4: | ureX2301 | 1 - 226 | ( 226 aa) | 99% |
| Sequence 5: | ureX390 | 1 - 226 | ( 226 aa) | 99% |
| Sequence 6: | A felis | 1 - 237 | ( 237 aa) | 50% |
| Sequence 7: | A pylori | 1 - 238 | ( 238 aa) | 52% |
| Sequence 8: | A heilman | 1 - 234 | ( 234 aa) | 54% |

Alignment type:    Global Protein
Parameters:        Mismatch 2;  Open Gap 4;  Extend Gap 1;  Conserv N

```
ureXCS1     1) vkltpkeqekfllyyagevarkrkaegiklnqpeaiayisahimdearrgkktvaqlmeeemhflkkdevmpgvgnmvpdlgvcatfpdgtklvtvnwpiepdehfkagevkfgcdkdie
ureXkuka    1) ............................................................e...........................................................
ureXDS4     1) ............................................................e...........................................................
ureX2301    1) .?..........................................................e...........................................................
ureX390     1) ............................................................e...........................................................
A felis     1) m......ld.lm.h...rl.eeal.r.v...yt.v.l..grv.ek.d.n.s.d..q.grtw...en.d..as.ihev.i..n..........iht.v.dngklap....ikne..t
A pylori    1) m......ld.lm.h...l.k..ek.i...yv.v.l...e..a...a.e..q.grtl.p.d.d..as.ihev.i.m..........ht..angklvp..-l.lkne..t
A heilman   1) m......ld.lm.h...l.kq..k.i...yt.v.l...ve..a...s.d..q.grtl.a.d....ah.ihev.i.g..........iht.v.agsdkl.pgevilkne..t ureXCS1   121) lnagkevtelevtnegpkslhvgshfhffeankikfdrekaygkridipsgntlrigagqtrkvqliplggskkvigmngivmniaderhkhkaldkakshgfi----------k
ureXkuka  121) ............................................................................................................e................
ureXDS4   121) ............................................................................................................................
ureX2301  121) ......................t.....................................................................................................
ureX390   121) ......................t.....................................................................................................
A felis   120) i..v..ais.k.k.k.drpvq........v.l.d..a.sfc......a..tav.fep.eeks.e..di..n.riy.f.s..drq..adg.klg.kr..ek..gsvncgceatkdk-q
A pylori  120) i.e..kavsvk.k.v.drpvqi.......v.rc.d.........tf.......a..tav.fep.eeks.e..di..nrrif.f.a..drq..nes.ki..hr..er..hgaksddnyvktike
A heilman 121) ....havq.k.k.k.drpvq.........v.l.d.............a..tav.fep.eekt.e..di..n.riy.f.a..drq..hdg.kl..kr..ekh..gtincgcdn-----
```

```
ureYCS1   (   ) hhgkakfdtsitfvskvayengvkekiglerqvlpvkncrnitkkdfkfndktakitvdpktfevfvdgklctskptsqvplaqrytff
ureYkuka  (480) ................................k..................n..h.....................e.........
ureYDS4   (480) ................................k..................n..h.....................a.c.......
ureY2301  (480) .....................................................h.....................a.c.......
ureY390   (480) ...............................................................................rvss..
ureY felis (481) ....n...n.....qa..ka.i..e...d..aap...........l....v..h.d.n.e.yk.k.....ev...aadels...l.nl.
B pylori  (481) ....y.an......qa..dk.i..e............mg...t..h.e.n.e.yh......ev...ank.s...lfsi.
B heilman (480) ........n.....q......i.he...q.v.....l....v..h.e.n.e.yk.k...nev..haadkls...l.nl.
```

Figure 1c (2)

SEQUENCE LISTING

```
<160> NUMBER OF SEQ ID NOS: 21

<210> SEQ ID NO 1
<211> LENGTH: 2883
<212> TYPE: DNA
<213> ORGANISM: Helicobacter felis
<220> FEATURE:
<221> NAME/KEY: CDS
<222> LOCATION: (206)..(886)
<220> FEATURE:
<221> NAME/KEY: CDS
<222> LOCATION: (897)..(2603)

<400> SEQUENCE: 1
rggragattt tccarcactt caagcacata ttgatcctgt gttgtgggtg gtaaattrcr      60
acttgttaat rctattatta attttttaat aattacttat tatcatatat aataatatta    120
ttacttatat taaaaagtta ataaaaagta acgaaattag gactataatc ccattgcctt    180
taaaatttaa cacaaggagt aatag gtg aaa ctc aca ccc aaa gag caa gaa     232
                              Val Lys Leu Thr Pro Lys Glu Gln Glu
                                1               5 aag ttc ttg tta tat tat gcg ggc gaa gtg gct aga aag cgc aaa gca     280
Lys Phe Leu Leu Tyr Tyr Ala Gly Glu Val Ala Arg Lys Arg Lys Ala
 10              15                  20                  25 gag ggc tta aag ctc aac caa ccc gaa gcc att gct tac att agt gcc     328
Glu Gly Leu Lys Leu Asn Gln Pro Glu Ala Ile Ala Tyr Ile Ser Ala
                30                  35                  40 cat att atg gac gaa gcg cgc cgt gga aaa aaa acc gtt gcc cag ctt     376
His Ile Met Asp Glu Ala Arg Arg Gly Lys Lys Thr Val Ala Gln Leu
             45                  50                  55 atg gaa gag tgc atg cac ttt ttg aaa aaa gat gaa gta atg ccc ggg     424
Met Glu Glu Cys Met His Phe Leu Lys Lys Asp Glu Val Met Pro Gly
         60                  65                  70 gtg ggt aat atg gtt ccc gat cta ggt gta gaa gcc acc ttt cct gat     472
```

```
Val Gly Asn Met Val Pro Asp Leu Gly Val Glu Ala Thr Phe Pro Asp
         75                  80                  85 ggt acg aaa ctt gta act gtg aat tgg ccc atc gaa cca gat gag cac      520
Gly Thr Lys Leu Val Thr Val Asn Trp Pro Ile Glu Pro Asp Glu His
 90                  95                 100                 105 ttc aaa gcg ggc gaa gtg aaa ttt ggt tgc gat aaa gac atc gag ctc      568
Phe Lys Ala Gly Glu Val Lys Phe Gly Cys Asp Lys Asp Ile Glu Leu
                110                 115                 120 aat gca ggc aaa gaa gta acc gaa ctt gag gtt act aat gaa ggg cct      616
Asn Ala Gly Lys Glu Val Thr Glu Leu Glu Val Thr Asn Glu Gly Pro
                125                 130                 135 aaa tcc ttg cat gtg ggt agc cat ttc cac ttc ttt gaa gct aac aag      664
Lys Ser Leu His Val Gly Ser His Phe His Phe Phe Glu Ala Asn Lys
            140                 145                 150 gca cta aaa ttc gat cgt gaa aaa gcc tat ggc aaa cgc cta gat att      712
Ala Leu Lys Phe Asp Arg Glu Lys Ala Tyr Gly Lys Arg Leu Asp Ile
        155                 160                 165 ccc tct ggc aac acg cta cgc att ggg gca gga caa acc cgc aaa gtg      760
Pro Ser Gly Asn Thr Leu Arg Ile Gly Ala Gly Gln Thr Arg Lys Val
170                 175                 180                 185 cag ttg att cct ctt ggt ggc agt aaa aaa gtg att ggc atg aac ggg      808
Gln Leu Ile Pro Leu Gly Gly Ser Lys Lys Val Ile Gly Met Asn Gly
                190                 195                 200 ctt gtg aat aac atc gcg gat gaa cgc cat aaa cat aaa gcg ctt gac      856
Leu Val Asn Asn Ile Ala Asp Glu Arg His Lys His Lys Ala Leu Asp
                205                 210                 215 aag gcg aaa tct cac gga ttt atc aag taa ggagactccc atg aaa atg      905
Lys Ala Lys Ser His Gly Phe Ile Lys             Met Lys Met
            220                 225                         230 aaa aaa caa gaa tat gta aat acc tac gga ccc acc aaa ggc gat aaa      953
Lys Lys Gln Glu Tyr Val Asn Thr Tyr Gly Pro Thr Lys Gly Asp Lys
                235                 240                 245 gtg cgc tta gga gat acc gat ctt tgg gca gaa gta gaa cat gac tat     1001
Val Arg Leu Gly Asp Thr Asp Leu Trp Ala Glu Val Glu His Asp Tyr
                250                 255                 260 acc acc tat ggc gaa gaa ctt aaa ttt ggc gcg ggt aaa act atc cgt     1049
Thr Thr Tyr Gly Glu Glu Leu Lys Phe Gly Ala Gly Lys Thr Ile Arg
            265                 270                 275 gag ggt atg ggt cag agc aat agc cct gat gaa aac acc cta gat tta     1097
Glu Gly Met Gly Gln Ser Asn Ser Pro Asp Glu Asn Thr Leu Asp Leu
        280                 285                 290 gtc atc act aac gcg atg att atc gac tac acc ggg att tac aaa gcc     1145
Val Ile Thr Asn Ala Met Ile Ile Asp Tyr Thr Gly Ile Tyr Lys Ala
295                 300                 305                 310 gac att ggg att aaa aac ggc aaa atc cat ggc att ggc aag gca gga     1193
Asp Ile Gly Ile Lys Asn Gly Lys Ile His Gly Ile Gly Lys Ala Gly
                315                 320                 325 aac aag gac atg caa gat ggc gta agc cct cat atg gtc gtg ggt gtg     1241
Asn Lys Asp Met Gln Asp Gly Val Ser Pro His Met Val Val Gly Val
                330                 335                 340 ggc aca gaa gca cta gca ggg gaa ggt atg att att acc gct ggg gga     1289
Gly Thr Glu Ala Leu Ala Gly Glu Gly Met Ile Ile Thr Ala Gly Gly
            345                 350                 355 atc gat tca cac acc cac ttc ctt tct cca caa caa ttc cct acc gct     1337
Ile Asp Ser His Thr His Phe Leu Ser Pro Gln Gln Phe Pro Thr Ala
        360                 365                 370 cta gcc aat ggc gtt aca acc atg ttt gga ggc ggc aca ggt cct gta     1385
Leu Ala Asn Gly Val Thr Thr Met Phe Gly Gly Gly Thr Gly Pro Val
375                 380                 385                 390
```

-continued

```
gat ggc acg aat gcg act act atc act ccg ggc aaa tgg aac ttg cac      1433
Asp Gly Thr Asn Ala Thr Thr Ile Thr Pro Gly Lys Trp Asn Leu His
                395                 400                 405 cgc atg ttg cgc gca gca gaa gag tat tct atg aat gtg ggc ttt ttg      1481
Arg Met Leu Arg Ala Ala Glu Glu Tyr Ser Met Asn Val Gly Phe Leu
    410                 415                 420 ggc aaa ggc aat agc tct agc aaa aaa caa ctt gta gaa caa gta gaa      1529
Gly Lys Gly Asn Ser Ser Ser Lys Lys Gln Leu Val Glu Gln Val Glu
425                 430                 435 gcg ggc gcg att ggt ttt aaa ttg cat gaa gac tgg ggc aca aca cca      1577
Ala Gly Ala Ile Gly Phe Lys Leu His Glu Asp Trp Gly Thr Thr Pro
    440                 445                 450 agt gcg atc gat cac tgc ttg agc gtg gca gat gaa tac gat gtg caa      1625
Ser Ala Ile Asp His Cys Leu Ser Val Ala Asp Glu Tyr Asp Val Gln
455                 460                 465                 470 gtt tgt atc cac acc gat aca gtc aat gag gca ggt tat gta gat gac      1673
Val Cys Ile His Thr Asp Thr Val Asn Glu Ala Gly Tyr Val Asp Asp
                475                 480                 485 acc cta aat gca atg aac ggg cgc gcc atc cat gcc tac cac att gag      1721
Thr Leu Asn Ala Met Asn Gly Arg Ala Ile His Ala Tyr His Ile Glu
                490                 495                 500 gga gcg ggt gga gga cac tca cct gat gtt atc acc atg gca ggc gag      1769
Gly Ala Gly Gly Gly His Ser Pro Asp Val Ile Thr Met Ala Gly Glu
    505                 510                 515 ctc aat att cta ccc tcc tcc acc acc ccc act att ccc tat acc att      1817
Leu Asn Ile Leu Pro Ser Ser Thr Thr Pro Thr Ile Pro Tyr Thr Ile
520                 525                 530 aat acg gtt gca gaa cac tta gac atg ctc atg aca tgc cac cac cta      1865
Asn Thr Val Ala Glu His Leu Asp Met Leu Met Thr Cys His His Leu
535                 540                 545                 550 gac aaa cgc atc cgc gag gat tta caa ttt tct caa agc cgt atc cgc      1913
Asp Lys Arg Ile Arg Glu Asp Leu Gln Phe Ser Gln Ser Arg Ile Arg
                555                 560                 565 ccc ggc tct atc gcg gct gaa gat gtg ctc cat gat atg ggt gtg atc      1961
Pro Gly Ser Ile Ala Ala Glu Asp Val Leu His Asp Met Gly Val Ile
        570                 575                 580 gcg atg aca agc tcg gat tcg caa gca atg ggg cgt gca ggc gaa gtg      2009
Ala Met Thr Ser Ser Asp Ser Gln Ala Met Gly Arg Ala Gly Glu Val
            585                 590                 595 att cct cga act tgg cag act gcg gat aag aat aaa aaa gaa ttt ggt      2057
Ile Pro Arg Thr Trp Gln Thr Ala Asp Lys Asn Lys Lys Glu Phe Gly
        600                 605                 610 aag ctt cct gaa gat ggc aaa gat aac gat aat ttc cgc att aag cgc      2105
Lys Leu Pro Glu Asp Gly Lys Asp Asn Asp Asn Phe Arg Ile Lys Arg
615                 620                 625                 630 tac atc tcc aaa tac act atc aac ccc gct ttg acc cac ggc gtg agc      2153
Tyr Ile Ser Lys Tyr Thr Ile Asn Pro Ala Leu Thr His Gly Val Ser
                635                 640                 645 gag tat atc ggc tct gtg gaa gag ggc aag atc gcc gac ttg gtg gtg      2201
Glu Tyr Ile Gly Ser Val Glu Glu Gly Lys Ile Ala Asp Leu Val Val
            650                 655                 660 tgg aat cct gcc ttt ttt ggc gta aaa ccc aaa atc gtg atc aaa ggc      2249
Trp Asn Pro Ala Phe Phe Gly Val Lys Pro Lys Ile Val Ile Lys Gly
            665                 670                 675 ggt atg gtg gtc ttc tct gaa atg ggc gat tct aac gcg tct gtg ccc      2297
Gly Met Val Val Phe Ser Glu Met Gly Asp Ser Asn Ala Ser Val Pro
    680                 685                 690 act ccc caa ccg gtt tat tac cgc gaa atg ttt ggg cat cac ggc aag      2345
Thr Pro Gln Pro Val Tyr Tyr Arg Glu Met Phe Gly His His Gly Lys
695                 700                 705                 710
```

```
gcg aaa ttt gac acc agc atc act ttt gtt tcc aaa gtc gcc tat gaa    2393
Ala Lys Phe Asp Thr Ser Ile Thr Phe Val Ser Lys Val Ala Tyr Glu
            715                 720                 725 aat ggc gtg aaa gaa aag ctg ggc tta gag cgc caa gtt cta ccg gtc    2441
Asn Gly Val Lys Glu Lys Leu Gly Leu Glu Arg Gln Val Leu Pro Val
            730                 735                 740 aaa aac tgc cgt aac atc acc aag aaa gac ttc aag ttc aac gac aaa    2489
Lys Asn Cys Arg Asn Ile Thr Lys Lys Asp Phe Lys Phe Asn Asp Lys
            745                 750                 755 acg gca aaa atc acc gtc gat ccg aaa acc ttc gag gtc ttt gta gat    2537
Thr Ala Lys Ile Thr Val Asp Pro Lys Thr Phe Glu Val Phe Val Asp
    760                 765                 770 ggc aaa ctc tgc acc tct aaa ccc acc tcg caa gtg cct cta gcc cag    2585
Gly Lys Leu Cys Thr Ser Lys Pro Thr Ser Gln Val Pro Leu Ala Gln
775                 780                 785                 790 cgc tac act ttc ttc tag gcacaatgcc ccctttgggg gcaggttatt           2633
Arg Tyr Thr Phe Phe
                795 ttaggaatct tcatcaaacg cacctgcaat cggtcttgcg tgtgcgatcg tgtcgcttta  2693 aaacaacttt tcatctttaa gcaatcgcca tttttaatta atttaattct tataattaat  2753 attatattat gccccctcat ttttaaagga gaattatgcg taggtctttg gtattgctat  2813 gtggggttg tttggtgctg ggcgcaaagg gtattgaaac ccatcgcctc aaaaaagtag   2873 aagccacagg                                                         2883

<210> SEQ ID NO 2
<211> LENGTH: 226
<212> TYPE: PRT
<213> ORGANISM: Helicobacter felis

<400> SEQUENCE: 2

Val Lys Leu Thr Pro Lys Glu Gln Glu Lys Phe Leu Leu Tyr Tyr Ala
 1               5                  10                  15

Gly Glu Val Ala Arg Lys Arg Lys Ala Glu Gly Leu Lys Leu Asn Gln
                20                  25                  30

Pro Glu Ala Ile Ala Tyr Ile Ser Ala His Ile Met Asp Glu Ala Arg
            35                  40                  45

Arg Gly Lys Lys Thr Val Ala Gln Leu Met Glu Glu Cys Met His Phe
        50                  55                  60

Leu Lys Lys Asp Glu Val Met Pro Gly Val Gly Asn Met Val Pro Asp
 65                  70                  75                  80

Leu Gly Val Glu Ala Thr Phe Pro Asp Gly Thr Lys Leu Val Thr Val
                85                  90                  95

Asn Trp Pro Ile Glu Pro Asp Glu His Phe Lys Ala Gly Glu Val Lys
            100                 105                 110

Phe Gly Cys Asp Lys Asp Ile Glu Leu Asn Ala Gly Lys Glu Val Thr
        115                 120                 125

Glu Leu Glu Val Thr Asn Glu Gly Pro Lys Ser Leu His Val Gly Ser
    130                 135                 140

His Phe His Phe Phe Glu Ala Asn Lys Ala Leu Lys Phe Asp Arg Glu
145                 150                 155                 160

Lys Ala Tyr Gly Lys Arg Leu Asp Ile Pro Ser Gly Asn Thr Leu Arg
                165                 170                 175

Ile Gly Ala Gly Gln Thr Arg Lys Val Gln Leu Ile Pro Leu Gly Gly
            180                 185                 190
```

```
Ser Lys Lys Val Ile Gly Met Asn Gly Leu Val Asn Asn Ile Ala Asp
        195                 200                 205

Glu Arg His Lys His Lys Ala Leu Asp Lys Ala Lys Ser His Gly Phe
    210                 215                 220

Ile Lys
225

<210> SEQ ID NO 3
<211> LENGTH: 568
<212> TYPE: PRT
<213> ORGANISM: Helicobacter felis

<400> SEQUENCE: 3

Met Lys Met Lys Lys Gln Glu Tyr Val Asn Thr Tyr Gly Pro Thr Lys
 1               5                  10                  15

Gly Asp Lys Val Arg Leu Gly Asp Thr Asp Leu Trp Ala Glu Val Glu
            20                  25                  30

His Asp Tyr Thr Thr Tyr Gly Glu Glu Leu Lys Phe Gly Ala Gly Lys
        35                  40                  45

Thr Ile Arg Glu Gly Met Gly Gln Ser Asn Ser Pro Asp Glu Asn Thr
    50                  55                  60

Leu Asp Leu Val Ile Thr Asn Ala Met Ile Ile Asp Tyr Thr Gly Ile
65                  70                  75                  80

Tyr Lys Ala Asp Ile Gly Ile Lys Asn Gly Lys Ile His Gly Ile Gly
                85                  90                  95

Lys Ala Gly Asn Lys Asp Met Gln Asp Gly Val Ser Pro His Met Val
            100                 105                 110

Val Gly Val Gly Thr Glu Ala Leu Ala Gly Glu Gly Met Ile Ile Thr
        115                 120                 125

Ala Gly Gly Ile Asp Ser His Thr His Phe Leu Ser Pro Gln Gln Phe
    130                 135                 140

Pro Thr Ala Leu Ala Asn Gly Val Thr Thr Met Phe Gly Gly Gly Thr
145                 150                 155                 160

Gly Pro Val Asp Gly Thr Asn Ala Thr Thr Ile Thr Pro Gly Lys Trp
                165                 170                 175

Asn Leu His Arg Met Leu Arg Ala Ala Glu Glu Tyr Ser Met Asn Val
            180                 185                 190

Gly Phe Leu Gly Lys Gly Asn Ser Ser Lys Lys Gln Leu Val Glu
        195                 200                 205

Gln Val Glu Ala Gly Ala Ile Gly Phe Lys Leu His Glu Asp Trp Gly
    210                 215                 220

Thr Thr Pro Ser Ala Ile Asp His Cys Leu Ser Val Ala Asp Glu Tyr
225                 230                 235                 240

Asp Val Gln Val Cys Ile His Thr Asp Thr Val Asn Glu Ala Gly Tyr
                245                 250                 255

Val Asp Asp Thr Leu Asn Ala Met Asn Gly Arg Ala Ile His Ala Tyr
            260                 265                 270

His Ile Glu Gly Ala Gly Gly Gly His Ser Pro Asp Val Ile Thr Met
        275                 280                 285

Ala Gly Glu Leu Asn Ile Leu Pro Ser Ser Thr Thr Pro Thr Ile Pro
    290                 295                 300

Tyr Thr Ile Asn Thr Val Ala Glu His Leu Asp Met Leu Met Thr Cys
305                 310                 315                 320

His His Leu Asp Lys Arg Ile Arg Glu Asp Leu Gln Phe Ser Gln Ser
                325                 330                 335
```

```
Arg Ile Arg Pro Gly Ser Ile Ala Ala Glu Asp Val Leu His Asp Met
        340                 345                 350
Gly Val Ile Ala Met Thr Ser Asp Ser Gln Ala Met Gly Arg Ala
            355                 360                 365
Gly Glu Val Ile Pro Arg Thr Trp Gln Thr Ala Asp Lys Asn Lys Lys
    370                 375                 380
Glu Phe Gly Lys Leu Pro Glu Asp Gly Lys Asp Asn Asp Asn Phe Arg
385                 390                 395                 400
Ile Lys Arg Tyr Ile Ser Lys Tyr Thr Ile Asn Pro Ala Leu Thr His
                405                 410                 415
Gly Val Ser Glu Tyr Ile Gly Ser Val Glu Gly Lys Ile Ala Asp
            420                 425                 430
Leu Val Val Trp Asn Pro Ala Phe Phe Gly Val Lys Pro Lys Ile Val
                435                 440                 445
Ile Lys Gly Gly Met Val Val Phe Ser Glu Met Gly Asp Ser Asn Ala
        450                 455                 460
Ser Val Pro Thr Pro Gln Pro Val Tyr Tyr Arg Glu Met Phe Gly His
465                 470                 475                 480
His Gly Lys Ala Lys Phe Asp Thr Ser Ile Thr Phe Val Ser Lys Val
                485                 490                 495
Ala Tyr Glu Asn Gly Val Lys Glu Lys Leu Gly Leu Glu Arg Gln Val
            500                 505                 510
Leu Pro Val Lys Asn Cys Arg Asn Ile Thr Lys Lys Asp Phe Lys Phe
                515                 520                 525
Asn Asp Lys Thr Ala Lys Ile Thr Val Asp Pro Lys Thr Phe Glu Val
        530                 535                 540
Phe Val Asp Gly Lys Leu Cys Thr Ser Lys Pro Thr Ser Gln Val Pro
545                 550                 555                 560
Leu Ala Gln Arg Tyr Thr Phe Phe
                565

<210> SEQ ID NO 4
<211> LENGTH: 2405
<212> TYPE: DNA
<213> ORGANISM: Helicobacter felis
<220> FEATURE:
<221> NAME/KEY: CDS
<222> LOCATION: (1)..(681)
<220> FEATURE:
<221> NAME/KEY: CDS
<222> LOCATION: (692)..(2398)

<400> SEQUENCE: 4 gtg aaa ctc aca ccc aaa gag caa gaa aag ttc ttg tta tat tat gcg      48
Val Lys Leu Thr Pro Lys Glu Gln Glu Lys Phe Leu Leu Tyr Tyr Ala
 1               5                  10                  15 ggc gaa gtg gct aga aag cgc aaa gca gag ggc tta aag ctc aat caa     96
Gly Glu Val Ala Arg Lys Arg Lys Ala Glu Gly Leu Lys Leu Asn Gln
                20                  25                  30 ccc gaa gcc att gcc tac att agt gcc cat att atg gac gag gcg cgc    144
Pro Glu Ala Ile Ala Tyr Ile Ser Ala His Ile Met Asp Glu Ala Arg
            35                  40                  45 cgt ggc aaa aaa acc gtt gct gaa ctt atg gaa gaa tgt atg cac ttt    192
Arg Gly Lys Lys Thr Val Ala Glu Leu Met Glu Glu Cys Met His Phe
        50                  55                  60 ttg aaa aaa gat gag gtg atg ccc ggt gtg ggg aat atg gtc cct gat    240
Leu Lys Lys Asp Glu Val Met Pro Gly Val Gly Asn Met Val Pro Asp
 65                  70                  75                  80
```

-continued

| | |
|---|---|
| ttg ggc gta gaa gcc act ttc ccc gat ggc acc aaa ctc gta acc gtg<br>Leu Gly Val Glu Ala Thr Phe Pro Asp Gly Thr Lys Leu Val Thr Val<br>                            85                                 90                              95 | 288 |
| aat tgg ccc att gaa cct gat gaa cac ttt aaa gcc ggt gaa gtg aaa<br>Asn Trp Pro Ile Glu Pro Asp Glu His Phe Lys Ala Gly Glu Val Lys<br>                 100                            105                          110 | 336 |
| ttt ggc tgt gat aaa gac att gag ctc aac gcg ggt aag gaa gtt acc<br>Phe Gly Cys Asp Lys Asp Ile Glu Leu Asn Ala Gly Lys Glu Val Thr<br>               115                            120                        125 | 384 |
| gag ctt gaa gtt acc aac gaa gga cct aaa tcc ttg cat gtg ggt agc<br>Glu Leu Glu Val Thr Asn Glu Gly Pro Lys Ser Leu His Val Gly Ser<br>130                           135                                140 | 432 |
| cat ttc cac ttc ttt gaa acc aac aag gca ttg aaa ttc gat cgg gaa<br>His Phe His Phe Phe Glu Thr Asn Lys Ala Leu Lys Phe Asp Arg Glu<br>145                           150                              155                        160 | 480 |
| aaa gcc tat ggc aaa cgc cta gat att ccc tct ggc aac acg cta cgc<br>Lys Ala Tyr Gly Lys Arg Leu Asp Ile Pro Ser Gly Asn Thr Leu Arg<br>                     165                            170                          175 | 528 |
| att ggg gca gga caa acc cgt aaa gtg cag tta atc cct ctt ggc ggt<br>Ile Gly Ala Gly Gln Thr Arg Lys Val Gln Leu Ile Pro Leu Gly Gly<br>               180                            185                        190 | 576 |
| agt aaa aaa gtg att ggc atg aac ggg ctt gtg aat aat att gcg gac<br>Ser Lys Lys Val Ile Gly Met Asn Gly Leu Val Asn Asn Ile Ala Asp<br>             195                            200                        205 | 624 |
| gaa cgc cat aaa cac aaa gca cta gac aag gca aaa tct cac gga ttc<br>Glu Arg His Lys His Lys Ala Leu Asp Lys Ala Lys Ser His Gly Phe<br>210                         215                              220 | 672 |
| atc aag taa ggagactccc atg aaa atg aaa aaa caa gag tat gta aac<br>Ile Lys                      Met Lys Met Lys Lys Gln Glu Tyr Val Asn<br>225                                     230                              235 | 721 |
| acc tac gga ccc acc aca ggc gat aaa gtg cgc tta gga gat acc gat<br>Thr Tyr Gly Pro Thr Thr Gly Asp Lys Val Arg Leu Gly Asp Thr Asp<br>               240                            245                        250 | 769 |
| ctt tgg gca gaa gta gaa cat gac tat acc act tat ggc gaa gag ctc<br>Leu Trp Ala Glu Val Glu His Asp Tyr Thr Thr Tyr Gly Glu Glu Leu<br>255                           260                              265 | 817 |
| aaa ttt ggc gcg ggt aaa act atc cgt gag ggt atg ggt cag agc aat<br>Lys Phe Gly Ala Gly Lys Thr Ile Arg Glu Gly Met Gly Gln Ser Asn<br>270                         275                              280                        285 | 865 |
| agc cca gat gaa aac acc tta gat tta gtg atc acc aac gcg atg att<br>Ser Pro Asp Glu Asn Thr Leu Asp Leu Val Ile Thr Asn Ala Met Ile<br>                     290                            295                          300 | 913 |
| atc gac tac acc ggg att tat aaa gcc gac att ggt att aaa aat ggc<br>Ile Asp Tyr Thr Gly Ile Tyr Lys Ala Asp Ile Gly Ile Lys Asn Gly<br>               305                            310                        315 | 961 |
| aaa atc cat ggt att ggc aag gcg ggg aac aaa gac atg caa gat ggc<br>Lys Ile His Gly Ile Gly Lys Ala Gly Asn Lys Asp Met Gln Asp Gly<br>             320                            325                        330 | 1009 |
| gta agc cct cat atg gtc gtg ggt gtg ggc aca gaa gca cta gca ggg<br>Val Ser Pro His Met Val Val Gly Val Gly Thr Glu Ala Leu Ala Gly<br>335                           340                              345 | 1057 |
| gaa ggt atg att att acc gct ggg ggg atc gat tcg cac acc cac ttc<br>Glu Gly Met Ile Ile Thr Ala Gly Gly Ile Asp Ser His Thr His Phe<br>350                         355                              360                        365 | 1105 |
| ctc tct ccc caa caa ttc cct acc gct cta gcc aat ggt gtt aca acc<br>Leu Ser Pro Gln Gln Phe Pro Thr Ala Leu Ala Asn Gly Val Thr Thr<br>                     370                            375                          380 | 1153 |
| atg ttt gga ggt ggc aca ggt ccg gta gat ggc acg aat gcg acc acc<br>Met Phe Gly Gly Gly Thr Gly Pro Val Asp Gly Thr Asn Ala Thr Thr | 1201 |

-continued

|  |  |  |  |  |  |  |  |  |  |  |  |  |  |  |  |
|---|---|---|---|---|---|---|---|---|---|---|---|---|---|---|---|
|  |  | 385 |  |  |  | 390 |  |  |  | 395 |  |  |  |  |  |
| atc | act | ccg | ggc | aaa | tgg | aac | ttg | cac | cgc | atg | ttg | cgc | gca | gct | gaa | 1249 |
| Ile | Thr | Pro | Gly | Lys | Trp | Asn | Leu | His | Arg | Met | Leu | Arg | Ala | Ala | Glu |  |
|  |  | 400 |  |  |  | 405 |  |  |  | 410 |  |  |  |  |  |
| gag | tat | tct | atg | aat | gtg | ggc | ttt | ttg | ggc | aaa | ggc | aat | agc | tcc | agt | 1297 |
| Glu | Tyr | Ser | Met | Asn | Val | Gly | Phe | Leu | Gly | Lys | Gly | Asn | Ser | Ser | Ser |  |
|  | 415 |  |  |  |  | 420 |  |  |  |  | 425 |  |  |  |  |
| aaa | aaa | caa | ctc | gta | gaa | caa | gta | gaa | gcg | ggc | gcg | att | ggc | ttt | aaa | 1345 |
| Lys | Lys | Gln | Leu | Val | Glu | Gln | Val | Glu | Ala | Gly | Ala | Ile | Gly | Phe | Lys |  |
| 430 |  |  |  |  | 435 |  |  |  |  | 440 |  |  |  |  | 445 |
| ttg | cat | gaa | gac | tgg | ggc | aca | aca | cca | agt | gcg | atc | gat | cac | tgc | ttg | 1393 |
| Leu | His | Glu | Asp | Trp | Gly | Thr | Thr | Pro | Ser | Ala | Ile | Asp | His | Cys | Leu |  |
|  |  |  |  | 450 |  |  |  |  | 455 |  |  |  |  | 460 |  |
| agc | gta | gca | gat | gaa | tac | gat | gtg | caa | gtt | tgt | atc | cac | acc | gat | acg | 1441 |
| Ser | Val | Ala | Asp | Glu | Tyr | Asp | Val | Gln | Val | Cys | Ile | His | Thr | Asp | Thr |  |
|  |  |  | 465 |  |  |  |  | 470 |  |  |  |  | 475 |  |  |
| gtc | aat | gag | gca | ggt | tat | gta | gat | gac | acc | cta | aat | gcg | atg | aac | ggg | 1489 |
| Val | Asn | Glu | Ala | Gly | Tyr | Val | Asp | Asp | Thr | Leu | Asn | Ala | Met | Asn | Gly |  |
|  |  |  | 480 |  |  |  |  | 485 |  |  |  |  | 490 |  |  |
| cgc | gcc | atc | cat | gcc | tac | cac | att | gag | gga | gcg | ggc | gga | gga | cac | tca | 1537 |
| Arg | Ala | Ile | His | Ala | Tyr | His | Ile | Glu | Gly | Ala | Gly | Gly | Gly | His | Ser |  |
|  | 495 |  |  |  |  | 500 |  |  |  |  | 505 |  |  |  |  |
| cct | gat | gtt | atc | acc | atg | gca | ggc | gag | ctc | aat | att | cta | ccc | tcc | tcc | 1585 |
| Pro | Asp | Val | Ile | Thr | Met | Ala | Gly | Glu | Leu | Asn | Ile | Leu | Pro | Ser | Ser |  |
| 510 |  |  |  |  | 515 |  |  |  |  | 520 |  |  |  |  | 525 |
| acc | acc | ccc | act | att | ccc | tat | acc | att | aat | acg | gtt | gca | gaa | cac | tta | 1633 |
| Thr | Thr | Pro | Thr | Ile | Pro | Tyr | Thr | Ile | Asn | Thr | Val | Ala | Glu | His | Leu |  |
|  |  |  |  | 530 |  |  |  |  | 535 |  |  |  |  | 540 |  |
| gac | atg | ctc | atg | acc | tgc | cac | cac | cta | gac | aaa | cgc | atc | cgc | gag | gat | 1681 |
| Asp | Met | Leu | Met | Thr | Cys | His | His | Leu | Asp | Lys | Arg | Ile | Arg | Glu | Asp |  |
|  |  |  | 545 |  |  |  |  | 550 |  |  |  |  | 555 |  |  |
| ctc | cag | ttt | tcc | caa | agc | cgt | atc | cgc | ccc | ggc | tct | att | gcc | gct | gaa | 1729 |
| Leu | Gln | Phe | Ser | Gln | Ser | Arg | Ile | Arg | Pro | Gly | Ser | Ile | Ala | Ala | Glu |  |
|  |  |  | 560 |  |  |  |  | 565 |  |  |  |  | 570 |  |  |
| gat | gtg | ctc | cat | gat | att | ggc | gtg | atc | gcg | atg | aca | agc | tcg | gat | tcg | 1777 |
| Asp | Val | Leu | His | Asp | Ile | Gly | Val | Ile | Ala | Met | Thr | Ser | Ser | Asp | Ser |  |
|  | 575 |  |  |  |  | 580 |  |  |  |  | 585 |  |  |  |  |
| caa | gca | atg | ggg | cgc | gct | ggg | gaa | gtg | att | cct | aga | act | tgg | caa | act | 1825 |
| Gln | Ala | Met | Gly | Arg | Ala | Gly | Glu | Val | Ile | Pro | Arg | Thr | Trp | Gln | Thr |  |
| 590 |  |  |  |  | 595 |  |  |  |  | 600 |  |  |  |  | 605 |
| gca | gac | aag | aat | aaa | aaa | gaa | ttt | ggt | aag | ctt | cct | gaa | gat | ggt | gca | 1873 |
| Ala | Asp | Lys | Asn | Lys | Lys | Glu | Phe | Gly | Lys | Leu | Pro | Glu | Asp | Gly | Ala |  |
|  |  |  |  | 610 |  |  |  |  | 615 |  |  |  |  | 620 |  |
| gat | aat | gac | aac | ttc | cgc | atc | aaa | cgc | tat | atc | tcc | aaa | tac | acc | att | 1921 |
| Asp | Asn | Asp | Asn | Phe | Arg | Ile | Lys | Arg | Tyr | Ile | Ser | Lys | Tyr | Thr | Ile |  |
|  |  |  | 625 |  |  |  |  | 630 |  |  |  |  | 635 |  |  |
| aat | ccc | gct | ttg | acc | cat | ggc | gtg | agc | gag | tat | atc | ggc | tct | gtg | gaa | 1969 |
| Asn | Pro | Ala | Leu | Thr | His | Gly | Val | Ser | Glu | Tyr | Ile | Gly | Ser | Val | Glu |  |
|  |  | 640 |  |  |  |  | 645 |  |  |  |  | 650 |  |  |  |
| gag | ggc | aag | atc | gcc | gac | ttg | gtg | gtg | tgg | aat | cct | gct | ttc | ttt | ggt | 2017 |
| Glu | Gly | Lys | Ile | Ala | Asp | Leu | Val | Val | Trp | Asn | Pro | Ala | Phe | Phe | Gly |  |
|  | 655 |  |  |  |  | 660 |  |  |  |  | 665 |  |  |  |  |
| gta | aaa | ccc | aaa | atc | gtg | atc | aaa | ggc | ggt | atg | gtg | gtg | ttc | tct | gaa | 2065 |
| Val | Lys | Pro | Lys | Ile | Val | Ile | Lys | Gly | Gly | Met | Val | Val | Phe | Ser | Glu |  |
| 670 |  |  |  |  | 675 |  |  |  |  | 680 |  |  |  |  | 685 |
| atg | ggc | gat | tct | aac | gcg | tct | gtg | ccc | aca | cct | cag | ccg | gtt | tat | tac | 2113 |
| Met | Gly | Asp | Ser | Asn | Ala | Ser | Val | Pro | Thr | Pro | Gln | Pro | Val | Tyr | Tyr |  |
|  |  |  |  | 690 |  |  |  |  | 695 |  |  |  |  | 700 |  |
| cgc | gaa | atg | ttt | ggg | cat | cac | ggc | aag | gcg | aaa | ttt | gac | acc | agc | atc | 2161 |

-continued

```
                Arg Glu Met Phe Gly His His Gly Lys Ala Lys Phe Asp Thr Ser Ile
                            705                 710                 715 act ttt gtt tcc aaa gtc gcc tat gaa aat ggc gtg aaa gaa aaa cta       2209
Thr Phe Val Ser Lys Val Ala Tyr Glu Asn Gly Val Lys Glu Lys Leu
            720                 725                 730 ggc tta gag cgc aag gtg cta ccc gtg aaa aac tgc cgc aac atc act       2257
Gly Leu Glu Arg Lys Val Leu Pro Val Lys Asn Cys Arg Asn Ile Thr
735                 740                 745 aag aaa gac ttc aaa ttc aac aac aag acg gcg cat atc act gtc gat       2305
Lys Lys Asp Phe Lys Phe Asn Asn Lys Thr Ala His Ile Thr Val Asp
750                 755                 760                 765 cct aaa acc ttc gag gtc ttt gta gat ggc aaa ctc tgc acc tct aaa       2353
Pro Lys Thr Phe Glu Val Phe Val Asp Gly Lys Leu Cys Thr Ser Lys
                770                 775                 780 ccc gcc tct gaa gtg cct cta gcc caa cgc tac act ttc ttc tag           2398
Pro Ala Ser Glu Val Pro Leu Ala Gln Arg Tyr Thr Phe Phe
                785                 790                 795 gcacaat                                                                2405
```

<210> SEQ ID NO 5
<211> LENGTH: 226
<212> TYPE: PRT
<213> ORGANISM: Helicobacter felis

<400> SEQUENCE: 5

```
Val Lys Leu Thr Pro Lys Glu Gln Glu Lys Phe Leu Leu Tyr Tyr Ala
  1               5                  10                  15

Gly Glu Val Ala Arg Lys Arg Lys Ala Glu Gly Leu Lys Leu Asn Gln
                 20                  25                  30

Pro Glu Ala Ile Ala Tyr Ile Ser Ala His Ile Met Asp Glu Ala Arg
             35                  40                  45

Arg Gly Lys Lys Thr Val Ala Glu Leu Met Glu Glu Cys Met His Phe
         50                  55                  60

Leu Lys Lys Asp Glu Val Met Pro Gly Val Gly Asn Met Val Pro Asp
 65                  70                  75                  80

Leu Gly Val Glu Ala Thr Phe Pro Asp Gly Thr Lys Leu Val Thr Val
                 85                  90                  95

Asn Trp Pro Ile Glu Pro Asp Glu His Phe Lys Ala Gly Glu Val Lys
            100                 105                 110

Phe Gly Cys Asp Lys Asp Ile Glu Leu Asn Ala Gly Lys Glu Val Thr
        115                 120                 125

Glu Leu Glu Val Thr Asn Glu Gly Pro Lys Ser Leu His Val Gly Ser
    130                 135                 140

His Phe His Phe Glu Thr Asn Lys Ala Leu Lys Phe Asp Arg Glu
145                 150                 155                 160

Lys Ala Tyr Gly Lys Arg Leu Asp Ile Pro Ser Gly Asn Thr Leu Arg
                165                 170                 175

Ile Gly Ala Gly Gln Thr Arg Lys Val Gln Leu Ile Pro Leu Gly Gly
            180                 185                 190

Ser Lys Lys Val Ile Gly Met Asn Gly Leu Val Asn Asn Ile Ala Asp
        195                 200                 205

Glu Arg His Lys His Lys Ala Leu Asp Lys Ala Lys Ser His Gly Phe
    210                 215                 220

Ile Lys
225
```

-continued

<210> SEQ ID NO 6
<211> LENGTH: 568
<212> TYPE: PRT
<213> ORGANISM: Helicobacter felis

<400> SEQUENCE: 6

```
Met Lys Met Lys Lys Gln Glu Tyr Val Asn Thr Tyr Gly Pro Thr Thr
 1               5                  10                  15

Gly Asp Lys Val Arg Leu Gly Asp Thr Asp Leu Trp Ala Glu Val Glu
             20                  25                  30

His Asp Tyr Thr Thr Tyr Gly Glu Glu Leu Lys Phe Gly Ala Gly Lys
         35                  40                  45

Thr Ile Arg Glu Gly Met Gly Gln Ser Asn Ser Pro Asp Glu Asn Thr
     50                  55                  60

Leu Asp Leu Val Ile Thr Asn Ala Met Ile Ile Asp Tyr Thr Gly Ile
 65                  70                  75                  80

Tyr Lys Ala Asp Ile Gly Ile Lys Asn Gly Lys Ile His Gly Ile Gly
                 85                  90                  95

Lys Ala Gly Asn Lys Asp Met Gln Asp Gly Val Ser Pro His Met Val
            100                 105                 110

Val Gly Val Gly Thr Glu Ala Leu Ala Gly Glu Gly Met Ile Ile Thr
        115                 120                 125

Ala Gly Gly Ile Asp Ser His Thr His Phe Leu Ser Pro Gln Gln Phe
    130                 135                 140

Pro Thr Ala Leu Ala Asn Gly Val Thr Thr Met Phe Gly Gly Gly Thr
145                 150                 155                 160

Gly Pro Val Asp Gly Thr Asn Ala Thr Thr Ile Thr Pro Gly Lys Trp
                165                 170                 175

Asn Leu His Arg Met Leu Arg Ala Ala Glu Glu Tyr Ser Met Asn Val
            180                 185                 190

Gly Phe Leu Gly Lys Gly Asn Ser Ser Lys Lys Gln Leu Val Glu
        195                 200                 205

Gln Val Glu Ala Gly Ala Ile Gly Phe Lys Leu His Glu Asp Trp Gly
    210                 215                 220

Thr Thr Pro Ser Ala Ile Asp His Cys Leu Ser Val Ala Asp Glu Tyr
225                 230                 235                 240

Asp Val Gln Val Cys Ile His Thr Asp Thr Val Asn Glu Ala Gly Tyr
                245                 250                 255

Val Asp Asp Thr Leu Asn Ala Met Asn Gly Arg Ala Ile His Ala Tyr
            260                 265                 270

His Ile Glu Gly Ala Gly Gly Gly His Ser Pro Asp Val Ile Thr Met
        275                 280                 285

Ala Gly Glu Leu Asn Ile Leu Pro Ser Ser Thr Thr Pro Thr Ile Pro
    290                 295                 300

Tyr Thr Ile Asn Thr Val Ala Glu His Leu Asp Met Leu Met Thr Cys
305                 310                 315                 320

His His Leu Asp Lys Arg Ile Arg Glu Asp Leu Gln Phe Ser Gln Ser
                325                 330                 335

Arg Ile Arg Pro Gly Ser Ile Ala Ala Glu Asp Val Leu His Asp Ile
            340                 345                 350

Gly Val Ile Ala Met Thr Ser Ser Asp Ser Gln Ala Met Gly Arg Ala
        355                 360                 365

Gly Glu Val Ile Pro Arg Thr Trp Gln Thr Ala Asp Lys Asn Lys Lys
    370                 375                 380
```

```
Glu Phe Gly Lys Leu Pro Glu Asp Gly Ala Asp Asn Asp Asn Phe Arg
385                 390                 395                 400

Ile Lys Arg Tyr Ile Ser Lys Tyr Thr Ile Asn Pro Ala Leu Thr His
            405                 410                 415

Gly Val Ser Glu Tyr Ile Gly Ser Val Glu Glu Gly Lys Ile Ala Asp
            420                 425                 430

Leu Val Val Trp Asn Pro Ala Phe Phe Gly Val Lys Pro Lys Ile Val
        435                 440                 445

Ile Lys Gly Gly Met Val Val Phe Ser Glu Met Gly Asp Ser Asn Ala
        450                 455                 460

Ser Val Pro Thr Pro Gln Pro Val Tyr Tyr Arg Glu Met Phe Gly His
465                 470                 475                 480

His Gly Lys Ala Lys Phe Asp Thr Ser Ile Thr Phe Val Ser Lys Val
            485                 490                 495

Ala Tyr Glu Asn Gly Val Lys Glu Lys Leu Gly Leu Glu Arg Lys Val
            500                 505                 510

Leu Pro Val Lys Asn Cys Arg Asn Ile Thr Lys Lys Asp Phe Lys Phe
        515                 520                 525

Asn Asn Lys Thr Ala His Ile Thr Val Asp Pro Lys Thr Phe Glu Val
        530                 535                 540

Phe Val Asp Gly Lys Leu Cys Thr Ser Lys Pro Ala Ser Glu Val Pro
545                 550                 555                 560

Leu Ala Gln Arg Tyr Thr Phe Phe
                565

<210> SEQ ID NO 7
<211> LENGTH: 2183
<212> TYPE: DNA
<213> ORGANISM: Helicobacter felis
<220> FEATURE:
<221> NAME/KEY: CDS
<222> LOCATION: (3)..(683)
<220> FEATURE:
<221> NAME/KEY: CDS
<222> LOCATION: (694)..(2181)

<400> SEQUENCE: 7 tc gtg aaa ctc aca ccc aaa gag caa gaa aag ttc ttg tta tat tat        47
   Val Lys Leu Thr Pro Lys Glu Gln Glu Lys Phe Leu Leu Tyr Tyr
    1               5                  10                  15 gcg ggc gaa gtg gct aga aag cgc aaa gca gag ggc tta aag ctc aat       95
Ala Gly Glu Val Ala Arg Lys Arg Lys Ala Glu Gly Leu Lys Leu Asn
                20                  25                  30 caa ccc gaa gcc att gcc tac att agt gcc cat att atg gac gag gcg      143
Gln Pro Glu Ala Ile Ala Tyr Ile Ser Ala His Ile Met Asp Glu Ala
            35                  40                  45 cgc cgt ggc aaa aaa acc gtt gct gaa ctt atg gaa gaa tgt atg cac      191
Arg Arg Gly Lys Lys Thr Val Ala Glu Leu Met Glu Glu Cys Met His
    50                  55                  60 ttt ttg aaa aaa gat gag gtg atg ccc ggt gtg ggg aat atg gtc cct      239
Phe Leu Lys Lys Asp Glu Val Met Pro Gly Val Gly Asn Met Val Pro
65                  70                  75 gat ttg ggc gta gaa gcc act ttc ccc gat ggc acc aaa ctc gta acc      287
Asp Leu Gly Val Glu Ala Thr Phe Pro Asp Gly Thr Lys Leu Val Thr
    80                  85                  90                  95 gtg aat tgg ccc att gaa cct gat gaa cac ttt aaa gcc ggt gaa gtg      335
Val Asn Trp Pro Ile Glu Pro Asp Glu His Phe Lys Ala Gly Glu Val
                100                 105                 110 aaa ttt ggc tgt gat aaa gac att gag ctc aac gtg ggt aag gaa gtt      383
```

-continued

```
Lys Phe Gly Cys Asp Lys Asp Ile Glu Leu Asn Val Gly Lys Glu Val
            115                 120                 125 acc gag ctt gaa gtt acc aac gaa gga cct aaa tcc ttg cat gtg ggt      431
Thr Glu Leu Glu Val Thr Asn Glu Gly Pro Lys Ser Leu His Val Gly
        130                 135                 140 agc cat ttc cac ttc ttt gaa acc aac aag gca ttg aaa ttc gat cgg      479
Ser His Phe His Phe Phe Glu Thr Asn Lys Ala Leu Lys Phe Asp Arg
    145                 150                 155 gaa aaa gcc tat ggc aaa cgc cta gat att ccc tct ggc aac acg cta      527
Glu Lys Ala Tyr Gly Lys Arg Leu Asp Ile Pro Ser Gly Asn Thr Leu
160                 165                 170                 175 cgc att ggg gca gga caa acc cgt aaa gtg cag tta atc cct ctt ggc      575
Arg Ile Gly Ala Gly Gln Thr Arg Lys Val Gln Leu Ile Pro Leu Gly
            180                 185                 190 ggt agt aaa aaa gtg att ggc atg aac ggg ctt gtg aat aat att gcg      623
Gly Ser Lys Lys Val Ile Gly Met Asn Gly Leu Val Asn Asn Ile Ala
        195                 200                 205 gac gaa cgc cat aaa cac aaa gca cta gac aag gca aaa tct cac gga      671
Asp Glu Arg His Lys His Lys Ala Leu Asp Lys Ala Lys Ser His Gly
    210                 215                 220 ttc atc aag taa ggagactccc atg aaa atg aaa aaa caa gag tat gta       720
Phe Ile Lys         Met Lys Met Lys Lys Gln Glu Tyr Val
225                             230                 235 aac acc tac gga ccc acc aca ggc gat aaa gtg cgc tta gga gat acc      768
Asn Thr Tyr Gly Pro Thr Thr Gly Asp Lys Val Arg Leu Gly Asp Thr
            240                 245                 250 gat ctt tgg gca gaa gta gaa cat gac tat acc act tat ggc gaa gag      816
Asp Leu Trp Ala Glu Val Glu His Asp Tyr Thr Thr Tyr Gly Glu Glu
        255                 260                 265 ctc aaa ttt ggc gcg ggt aaa act atc cgt gag ggt atg ggt cag agc      864
Leu Lys Phe Gly Ala Gly Lys Thr Ile Arg Glu Gly Met Gly Gln Ser
    270                 275                 280 aat agc cca gat gaa aac acc tta gat tta gtg atc acc aac gcg atg      912
Asn Ser Pro Asp Glu Asn Thr Leu Asp Leu Val Ile Thr Asn Ala Met
285                 290                 295                 300 att atc gac tac acc ggg att tat aaa gcc gac att ggt att aaa aat      960
Ile Ile Asp Tyr Thr Gly Ile Tyr Lys Ala Asp Ile Gly Ile Lys Asn
            305                 310                 315 ggc aaa atc cat ggt att ggc aag gcg ggg aac aaa gac atg caa gat     1008
Gly Lys Ile His Gly Ile Gly Lys Ala Gly Asn Lys Asp Met Gln Asp
        320                 325                 330 ggc gta agc cct cat atg gtc gtg ggt gtg ggc aca gaa gca cta gca     1056
Gly Val Ser Pro His Met Val Val Gly Val Gly Thr Glu Ala Leu Ala
    335                 340                 345 ggg gaa ggt atg att att acc gct ggg ggg atc gat tcg cac acc cac     1104
Gly Glu Gly Met Ile Ile Thr Ala Gly Gly Ile Asp Ser His Thr His
350                 355                 360 ttc ctc tct ccc caa caa ttc cct acc gct cta gcc aat ggt gtt aca     1152
Phe Leu Ser Pro Gln Gln Phe Pro Thr Ala Leu Ala Asn Gly Val Thr
            365                 370                 375                 380 acc atg ttt gga ggt ggc aca ggt ccg gta gat ggc acg aat gcg acc     1200
Thr Met Phe Gly Gly Gly Thr Gly Pro Val Asp Gly Thr Asn Ala Thr
        385                 390                 395 acc atc act ccg ggc aaa tgg aac ttg cac cgc atg ttg cgc gca gct     1248
Thr Ile Thr Pro Gly Lys Trp Asn Leu His Arg Met Leu Arg Ala Ala
    400                 405                 410 gaa gag tat tct atg aat gta ggc ttt ttg ggc aaa ggc aat agt tct     1296
Glu Glu Tyr Ser Met Asn Val Gly Phe Leu Gly Lys Gly Asn Ser Ser
415                 420                 425
```

```
agc aaa aaa caa ctt gta gaa caa gta gaa gcg ggc gcg att ggc ttt      1344
Ser Lys Lys Gln Leu Val Glu Gln Val Glu Ala Gly Ala Ile Gly Phe
    430                 435                 440 aaa ttg cat gaa gac tgg ggc aca aca cca agt gcg atc gat cac tgc      1392
Lys Leu His Glu Asp Trp Gly Thr Thr Pro Ser Ala Ile Asp His Cys
445                 450                 455                 460 ttg agc gtg gca gat gaa tac gat gtg caa gtt tgt atc cac acc gat      1440
Leu Ser Val Ala Asp Glu Tyr Asp Val Gln Val Cys Ile His Thr Asp
                465                 470                 475 acg gtc aat gag gca ggt tat gtg gat gac acc cta aat gca atg aac      1488
Thr Val Asn Glu Ala Gly Tyr Val Asp Asp Thr Leu Asn Ala Met Asn
            480                 485                 490 ggg cgc gcc atc cat gcc tac cac att gag gga gcg ggc gga gga cac      1536
Gly Arg Ala Ile His Ala Tyr His Ile Glu Gly Ala Gly Gly Gly His
        495                 500                 505 tca cct gat gtt atc acc atg gca ggc gag ctc aat att cta ccc tcc      1584
Ser Pro Asp Val Ile Thr Met Ala Gly Glu Leu Asn Ile Leu Pro Ser
    510                 515                 520 tcc acc acc ccc act att ccc tat acc att aat acg gtt gca gaa cac      1632
Ser Thr Thr Pro Thr Ile Pro Tyr Thr Ile Asn Thr Val Ala Glu His
525                 530                 535                 540 tta gac atg ctc atg acc tgc cac cac cta gat aag cgc atc cgc gag      1680
Leu Asp Met Leu Met Thr Cys His His Leu Asp Lys Arg Ile Arg Glu
                545                 550                 555 gat tta caa ttt tct caa agc cgt atc cgc ccc gga tct att gcc gct      1728
Asp Leu Gln Phe Ser Gln Ser Arg Ile Arg Pro Gly Ser Ile Ala Ala
            560                 565                 570 gag gat gtg ctc cat gat att ggc gtg atc gcg atg act agc tcc gat      1776
Glu Asp Val Leu His Asp Ile Gly Val Ile Ala Met Thr Ser Ser Asp
        575                 580                 585 tcg caa gca atg ggg cgc gct ggg gaa gtg att cct aga act tgg caa      1824
Ser Gln Ala Met Gly Arg Ala Gly Glu Val Ile Pro Arg Thr Trp Gln
    590                 595                 600 act gca gat aag aat aaa aaa gaa ttt ggt aag ctt cct gaa gat ggt      1872
Thr Ala Asp Lys Asn Lys Lys Glu Phe Gly Lys Leu Pro Glu Asp Gly
605                 610                 615                 620 gca gat aac gac aac ttc cgc atc aaa cgc tat atc tcc aaa tac acc      1920
Ala Asp Asn Asp Asn Phe Arg Ile Lys Arg Tyr Ile Ser Lys Tyr Thr
                625                 630                 635 att aat ccc gct ttg acc cat ggc gtg agc gag tat atc ggc tct gtg      1968
Ile Asn Pro Ala Leu Thr His Gly Val Ser Glu Tyr Ile Gly Ser Val
            640                 645                 650 gaa gag ggc aag atc gcc gac ttg gtg gtg tgg aat cct gcc ttt ttt      2016
Glu Glu Gly Lys Ile Ala Asp Leu Val Val Trp Asn Pro Ala Phe Phe
        655                 660                 665 ggc gtg aaa cct aag att gtg att aaa ggt ggc atg gtg gtc ttc tct      2064
Gly Val Lys Pro Lys Ile Val Ile Lys Gly Gly Met Val Val Phe Ser
    670                 675                 680 gaa atg ggc gat tct aac gcg tcc gtg ccc acg cct cag ccg gtt tat      2112
Glu Met Gly Asp Ser Asn Ala Ser Val Pro Thr Pro Gln Pro Val Tyr
685                 690                 695                 700 tac cgc gaa atg ttt ggg cac cac ggc aag gcg aaa ttt gac acc agc      2160
Tyr Arg Glu Met Phe Gly His His Gly Lys Ala Lys Phe Asp Thr Ser
                705                 710                 715 atc act ttt cgt gtc tca agc gg                                        2183
Ile Thr Phe Arg Val Ser Ser
            720

<210> SEQ ID NO 8
<211> LENGTH: 226
```

```
<212> TYPE: PRT
<213> ORGANISM: Helicobacter felis

<400> SEQUENCE: 8

Val Lys Leu Thr Pro Lys Glu Gln Lys Phe Leu Leu Tyr Tyr Ala
 1               5                  10                  15

Gly Glu Val Ala Arg Lys Arg Lys Ala Glu Gly Leu Lys Leu Asn Gln
            20                  25                  30

Pro Glu Ala Ile Ala Tyr Ile Ser Ala His Ile Met Asp Glu Ala Arg
        35                  40                  45

Arg Gly Lys Lys Thr Val Ala Glu Leu Met Glu Glu Cys Met His Phe
    50                  55                  60

Leu Lys Lys Asp Glu Val Met Pro Gly Val Gly Asn Met Val Pro Asp
65                  70                  75                  80

Leu Gly Val Glu Ala Thr Phe Pro Asp Gly Thr Lys Leu Val Thr Val
                85                  90                  95

Asn Trp Pro Ile Glu Pro Asp Glu His Phe Lys Ala Gly Glu Val Lys
            100                 105                 110

Phe Gly Cys Asp Lys Asp Ile Glu Leu Asn Val Gly Lys Glu Val Thr
        115                 120                 125

Glu Leu Glu Val Thr Asn Glu Gly Pro Lys Ser Leu His Val Gly Ser
    130                 135                 140

His Phe His Phe Phe Glu Thr Asn Lys Ala Leu Lys Phe Asp Arg Glu
145                 150                 155                 160

Lys Ala Tyr Gly Lys Arg Leu Asp Ile Pro Ser Gly Asn Thr Leu Arg
                165                 170                 175

Ile Gly Ala Gly Gln Thr Arg Lys Val Gln Leu Ile Pro Leu Gly Gly
            180                 185                 190

Ser Lys Lys Val Ile Gly Met Asn Gly Leu Val Asn Asn Ile Ala Asp
        195                 200                 205

Glu Arg His Lys His Lys Ala Leu Asp Lys Ala Lys Ser His Gly Phe
    210                 215                 220

Ile Lys
225

<210> SEQ ID NO 9
<211> LENGTH: 496
<212> TYPE: PRT
<213> ORGANISM: Helicobacter felis

<400> SEQUENCE: 9

Met Lys Met Lys Lys Gln Glu Tyr Val Asn Thr Tyr Gly Pro Thr Thr
 1               5                  10                  15

Gly Asp Lys Val Arg Leu Gly Asp Thr Asp Leu Trp Ala Glu Val Glu
            20                  25                  30

His Asp Tyr Thr Thr Tyr Gly Glu Glu Leu Lys Phe Gly Ala Gly Lys
        35                  40                  45

Thr Ile Arg Glu Gly Met Gly Gln Ser Asn Ser Pro Asp Glu Asn Thr
    50                  55                  60

Leu Asp Leu Val Ile Thr Asn Ala Met Ile Ile Asp Tyr Thr Gly Ile
65                  70                  75                  80

Tyr Lys Ala Asp Ile Gly Ile Lys Asn Gly Lys Ile His Gly Ile Gly
                85                  90                  95

Lys Ala Gly Asn Lys Asp Met Gln Asp Gly Val Ser Pro His Met Val
            100                 105                 110
```

```
Val Gly Val Gly Thr Glu Ala Leu Ala Gly Glu Gly Met Ile Ile Thr
            115                 120                 125

Ala Gly Gly Ile Asp Ser His Thr His Phe Leu Ser Pro Gln Gln Phe
            130                 135                 140

Pro Thr Ala Leu Ala Asn Gly Val Thr Thr Met Phe Gly Gly Gly Thr
145                 150                 155                 160

Gly Pro Val Asp Gly Thr Asn Ala Thr Thr Ile Thr Pro Gly Lys Trp
                165                 170                 175

Asn Leu His Arg Met Leu Arg Ala Ala Glu Glu Tyr Ser Met Asn Val
            180                 185                 190

Gly Phe Leu Gly Lys Gly Asn Ser Ser Lys Lys Gln Leu Val Glu
            195                 200                 205

Gln Val Glu Ala Gly Ala Ile Gly Phe Lys Leu His Glu Asp Trp Gly
            210                 215                 220

Thr Thr Pro Ser Ala Ile Asp His Cys Leu Ser Val Ala Asp Glu Tyr
225                 230                 235                 240

Asp Val Gln Val Cys Ile His Thr Asp Thr Val Asn Glu Ala Gly Tyr
                245                 250                 255

Val Asp Asp Thr Leu Asn Ala Met Asn Gly Arg Ala Ile His Ala Tyr
            260                 265                 270

His Ile Glu Gly Ala Gly Gly Gly His Ser Pro Asp Val Ile Thr Met
            275                 280                 285

Ala Gly Glu Leu Asn Ile Leu Pro Ser Ser Thr Thr Pro Thr Ile Pro
            290                 295                 300

Tyr Thr Ile Asn Thr Val Ala Glu His Leu Asp Met Leu Met Thr Cys
305                 310                 315                 320

His His Leu Asp Lys Arg Ile Arg Glu Asp Leu Gln Phe Ser Gln Ser
                325                 330                 335

Arg Ile Arg Pro Gly Ser Ile Ala Ala Glu Asp Val Leu His Asp Ile
            340                 345                 350

Gly Val Ile Ala Met Thr Ser Ser Asp Ser Gln Ala Met Gly Arg Ala
            355                 360                 365

Gly Glu Val Ile Pro Arg Thr Trp Gln Thr Ala Asp Lys Asn Lys Lys
370                 375                 380

Glu Phe Gly Lys Leu Pro Glu Asp Gly Ala Asp Asn Asp Asn Phe Arg
385                 390                 395                 400

Ile Lys Arg Tyr Ile Ser Lys Tyr Thr Ile Asn Pro Ala Leu Thr His
                405                 410                 415

Gly Val Ser Glu Tyr Ile Gly Ser Val Glu Glu Gly Lys Ile Ala Asp
            420                 425                 430

Leu Val Val Trp Asn Pro Ala Phe Phe Gly Val Lys Pro Lys Ile Val
            435                 440                 445

Ile Lys Gly Gly Met Val Val Phe Ser Glu Met Gly Asp Ser Asn Ala
450                 455                 460

Ser Val Pro Thr Pro Gln Pro Val Tyr Tyr Arg Glu Met Phe Gly His
465                 470                 475                 480

His Gly Lys Ala Lys Phe Asp Thr Ser Ile Thr Phe Arg Val Ser Ser
                485                 490                 495
```

<210> SEQ ID NO 10
<211> LENGTH: 2407
<212> TYPE: DNA
<213> ORGANISM: Helicobacter felis
<220> FEATURE:
<221> NAME/KEY: CDS

```
<222> LOCATION: (2)..(682)
<220> FEATURE:
<221> NAME/KEY: CDS
<222> LOCATION: (693)..(2399)

<400> SEQUENCE: 10 c gtg aaa ctc aca ccc aaa gag caa gaa aag ttc ttg tta tat tat gcg      49
  Val Lys Leu Thr Pro Lys Glu Gln Glu Lys Phe Leu Leu Tyr Tyr Ala
  1               5                   10                  15 ggc gaa gtg gct aga aag cgc aaa gcg gag ggc tta aag ctc aac caa        97
Gly Glu Val Ala Arg Lys Arg Lys Ala Glu Gly Leu Lys Leu Asn Gln
            20                  25                  30 ccc gaa gcc att gcc tac att agt gcc cat att atg gac gag gcg cgc       145
Pro Glu Ala Ile Ala Tyr Ile Ser Ala His Ile Met Asp Glu Ala Arg
        35                  40                  45 cgt ggc aaa aag acc gtt gcg gaa ctt atg gaa gag tgt atg cac ttt       193
Arg Gly Lys Lys Thr Val Ala Glu Leu Met Glu Glu Cys Met His Phe
50                  55                  60 ttg aaa aaa gac gag gtg atg ccc ggt gtg ggg aat atg gtc cct gat       241
Leu Lys Lys Asp Glu Val Met Pro Gly Val Gly Asn Met Val Pro Asp
65                  70                  75                  80 tta ggc gtg gaa gct act ttt ccc gat ggc acc aaa ctc gta acc gtg       289
Leu Gly Val Glu Ala Thr Phe Pro Asp Gly Thr Lys Leu Val Thr Val
                85                  90                  95 aat tgg ccc atc gaa ccc gat gaa cac ttc aaa gcg ggc gaa gtc aaa       337
Asn Trp Pro Ile Glu Pro Asp Glu His Phe Lys Ala Gly Glu Val Lys
            100                 105                 110 ttt ggc tgt gat aaa gac att gaa ctc aac gca ggt aag gaa gtt acc       385
Phe Gly Cys Asp Lys Asp Ile Glu Leu Asn Ala Gly Lys Glu Val Thr
        115                 120                 125 gaa cta gaa gtt acc aac gaa gga cct aaa tcc ttg cat gtg ggt agc       433
Glu Leu Glu Val Thr Asn Glu Gly Pro Lys Ser Leu His Val Gly Ser
130                 135                 140 cat ttc cac ttc ttt gaa gcc aac aag gca ttg aaa ttc gat cgg gaa       481
His Phe His Phe Phe Glu Ala Asn Lys Ala Leu Lys Phe Asp Arg Glu
145                 150                 155                 160 aaa gcc tat ggc aaa cgc cta gat att ccc tct ggc aac acg cta cgc       529
Lys Ala Tyr Gly Lys Arg Leu Asp Ile Pro Ser Gly Asn Thr Leu Arg
                165                 170                 175 att ggg gca gga caa acc cgt aaa gtg cag tta atc cct ctt ggc ggc       577
Ile Gly Ala Gly Gln Thr Arg Lys Val Gln Leu Ile Pro Leu Gly Gly
            180                 185                 190 agt aaa aaa gtg att ggc atg aac ggg ctt gtg aat aat att gca gat       625
Ser Lys Lys Val Ile Gly Met Asn Gly Leu Val Asn Asn Ile Ala Asp
        195                 200                 205 gaa cgc cat aaa cac aaa gcg tta gaa aaa gca aaa tct cac gga ttt       673
Glu Arg His Lys His Lys Ala Leu Glu Lys Ala Lys Ser His Gly Phe
210                 215                 220 atc aaa taa ggagactccc atg aaa atg aaa aaa caa gag tat gta aat       722
Ile Lys             Met Lys Met Lys Lys Gln Glu Tyr Val Asn
225                         230                 235 acc tac gga cct acc aca ggc gac aaa gtg cgc tta gga gat acc gat       770
Thr Tyr Gly Pro Thr Thr Gly Asp Lys Val Arg Leu Gly Asp Thr Asp
            240                 245                 250 ctt tgg gca gaa gta gaa cat gac tat acc act tat ggc gaa gag ctc       818
Leu Trp Ala Glu Val Glu His Asp Tyr Thr Thr Tyr Gly Glu Glu Leu
        255                 260                 265 aaa ttt ggc gcg ggt aaa act atc cgt gag ggc atg ggt cag agc aat       866
Lys Phe Gly Ala Gly Lys Thr Ile Arg Glu Gly Met Gly Gln Ser Asn
270                 275                 280                 285
```

-continued

| | |
|---|---|
| agt cca gat gaa aac acc cta gat tta gtc atc acc aac gcg atg att<br>Ser Pro Asp Glu Asn Thr Leu Asp Leu Val Ile Thr Asn Ala Met Ile<br>           290                    295                   300 | 914 |
| att gac tac acc ggg att tac aaa gcc gac att ggc att aaa aat ggc<br>Ile Asp Tyr Thr Gly Ile Tyr Lys Ala Asp Ile Gly Ile Lys Asn Gly<br>      305                    310                    315 | 962 |
| aaa atc cat ggc att ggc aag gca gga aac aag gac atg caa gat ggc<br>Lys Ile His Gly Ile Gly Lys Ala Gly Asn Lys Asp Met Gln Asp Gly<br>          320                    325                330 | 1010 |
| gta agc cct cat atg gtc gtg ggt gtg ggc aca gaa gca tta gca ggg<br>Val Ser Pro His Met Val Val Gly Val Gly Thr Glu Ala Leu Ala Gly<br>      335                    340                    345 | 1058 |
| gaa ggt atg att att acc gct ggg ggg atc gat tca cac acc cac ttc<br>Glu Gly Met Ile Ile Thr Ala Gly Gly Ile Asp Ser His Thr His Phe<br>350                    355                    360                   365 | 1106 |
| ctc tct cca caa caa ttc cct acc gct cta gcc aat ggc gtt aca acc<br>Leu Ser Pro Gln Gln Phe Pro Thr Ala Leu Ala Asn Gly Val Thr Thr<br>               370                    375                    380 | 1154 |
| atg ttt ggc ggt ggc aca ggt ccg gta gat ggc acg aat gcg act acc<br>Met Phe Gly Gly Gly Thr Gly Pro Val Asp Gly Thr Asn Ala Thr Thr<br>               385                    390                    395 | 1202 |
| atc act ccg ggc aaa tgg aac ttg cac cgc atg ttg cgc gca gct gaa<br>Ile Thr Pro Gly Lys Trp Asn Leu His Arg Met Leu Arg Ala Ala Glu<br>          400                    405                   410 | 1250 |
| gag tat tct atg aat gtg ggc ttt ttg ggc aaa ggc aat agc tcc agt<br>Glu Tyr Ser Met Asn Val Gly Phe Leu Gly Lys Gly Asn Ser Ser Ser<br>         415                    420                    425 | 1298 |
| aaa aaa caa ctt gta gaa caa ata gaa gcg ggc gcg atc ggc ttt aaa<br>Lys Lys Gln Leu Val Glu Gln Ile Glu Ala Gly Ala Ile Gly Phe Lys<br>430                    435                    440                   445 | 1346 |
| ttg cat gaa gac tgg ggc aca act cca agt gca atc gat cac tgc ttg<br>Leu His Glu Asp Trp Gly Thr Thr Pro Ser Ala Ile Asp His Cys Leu<br>                    450                    455                   460 | 1394 |
| agc gta gca gat gaa tac gat gtg caa gtt tgt atc cac acc gat acg<br>Ser Val Ala Asp Glu Tyr Asp Val Gln Val Cys Ile His Thr Asp Thr<br>               465                    470                    475 | 1442 |
| gtc aat gag gca ggt tat gta gat gac acc ctg aat gcg atg aac ggg<br>Val Asn Glu Ala Gly Tyr Val Asp Asp Thr Leu Asn Ala Met Asn Gly<br>          480                    485                   490 | 1490 |
| cgc gcc atc cat gcc tac cac att gag gga gcg ggc gga gga cac tca<br>Arg Ala Ile His Ala Tyr His Ile Glu Gly Ala Gly Gly Gly His Ser<br>             495                    500                    505 | 1538 |
| cct gat gtt atc acc atg gca ggc gag ctc aat att cta ccc tcc tcc<br>Pro Asp Val Ile Thr Met Ala Gly Glu Leu Asn Ile Leu Pro Ser Ser<br>510                    515                    520                   525 | 1586 |
| aca acc ccc act atc ccc tat acc att aat acg gtt gca gaa cac tta<br>Thr Thr Pro Thr Ile Pro Tyr Thr Ile Asn Thr Val Ala Glu His Leu<br>               530                    535                   540 | 1634 |
| gac atg ctc atg acc tgc cac cac cta gat aaa cgc atc cgc gag gat<br>Asp Met Leu Met Thr Cys His His Leu Asp Lys Arg Ile Arg Glu Asp<br>             545                    550                    555 | 1682 |
| tta caa ttt tcc caa agc cgt atc cgc ccc ggc tct atc gcc gct gaa<br>Leu Gln Phe Ser Gln Ser Arg Ile Arg Pro Gly Ser Ile Ala Ala Glu<br>          560                    565                   570 | 1730 |
| gat gtg ctc cat gat att ggc gtg atc gcg atg aca agc tcg gat tcg<br>Asp Val Leu His Asp Ile Gly Val Ile Ala Met Thr Ser Ser Asp Ser<br>             575                    580                   585 | 1778 |
| caa gca atg ggg cgc gct ggc gaa gtg att cct cga act tgg cag act<br>Gln Ala Met Gly Arg Ala Gly Glu Val Ile Pro Arg Thr Trp Gln Thr<br>590                    595                    600                   605 | 1826 |

```
gcg gat aag aat aaa aaa gaa ttt ggt aag ctt cct gaa gat agt gca      1874
Ala Asp Lys Asn Lys Lys Glu Phe Gly Lys Leu Pro Glu Asp Ser Ala
            610                 615                 620 gat aac gac aac ttc cgt atc aaa cgc tac atc tcc aaa tac act att      1922
Asp Asn Asp Asn Phe Arg Ile Lys Arg Tyr Ile Ser Lys Tyr Thr Ile
        625                 630                 635 aac ccc gct cta acc cat ggg gta agc gag tat atc ggc tct gtg gaa      1970
Asn Pro Ala Leu Thr His Gly Val Ser Glu Tyr Ile Gly Ser Val Glu
    640                 645                 650 gag ggc aaa atc gct gat ttg gtg gtg tgg aat cct gcc ttt ttt ggt      2018
Glu Gly Lys Ile Ala Asp Leu Val Val Trp Asn Pro Ala Phe Phe Gly
655                 660                 665 gtg aaa cct aag att gtg atc aaa ggc ggt atg gtg gtc ttc tct gaa      2066
Val Lys Pro Lys Ile Val Ile Lys Gly Gly Met Val Val Phe Ser Glu
670                 675                 680                 685 atg ggc gac tcc aac gcg tcc gtg cct aca cct cag ccg gtt tat tac      2114
Met Gly Asp Ser Asn Ala Ser Val Pro Thr Pro Gln Pro Val Tyr Tyr
                690                 695                 700 cgc gaa atg ttt ggg cat cac ggc aag gcg aaa ttt gac acc agc atc      2162
Arg Glu Met Phe Gly His His Gly Lys Ala Lys Phe Asp Thr Ser Ile
            705                 710                 715 act ttt gtt tcc aaa gtc gcc tat gaa aat ggc gtg aaa gaa aaa cta      2210
Thr Phe Val Ser Lys Val Ala Tyr Glu Asn Gly Val Lys Glu Lys Leu
        720                 725                 730 ggc tta gag cgc aag gtg cta ccc gtg aaa aac tgc cgc aac atc act      2258
Gly Leu Glu Arg Lys Val Leu Pro Val Lys Asn Cys Arg Asn Ile Thr
    735                 740                 745 aag aaa gac ttc aaa ttc aac aac aag acg gcg cat atc act gtc gat      2306
Lys Lys Asp Phe Lys Phe Asn Asn Lys Thr Ala His Ile Thr Val Asp
750                 755                 760                 765 cct aaa acc ttc gag gtc ttt gta gat ggc aaa ctc tgc acc tct aaa      2354
Pro Lys Thr Phe Glu Val Phe Val Asp Gly Lys Leu Cys Thr Ser Lys
                770                 775                 780 ccc gcc tct gaa gtg cct cta gcc cag cgc tac act ttc ttc tag         2399
Pro Ala Ser Glu Val Pro Leu Ala Gln Arg Tyr Thr Phe Phe
            785                 790                 795 gcncaatg                                                              2407

<210> SEQ ID NO 11
<211> LENGTH: 226
<212> TYPE: PRT
<213> ORGANISM: Helicobacter felis

<400> SEQUENCE: 11

Val Lys Leu Thr Pro Lys Glu Gln Glu Lys Phe Leu Leu Tyr Tyr Ala
 1               5                  10                  15

Gly Glu Val Ala Arg Lys Arg Lys Ala Glu Gly Leu Lys Leu Asn Gln
            20                  25                  30

Pro Glu Ala Ile Ala Tyr Ile Ser Ala His Ile Met Asp Glu Ala Arg
        35                  40                  45

Arg Gly Lys Lys Thr Val Ala Glu Leu Met Glu Glu Cys Met His Phe
    50                  55                  60

Leu Lys Lys Asp Glu Val Met Pro Gly Val Gly Asn Met Val Pro Asp
65                  70                  75                  80

Leu Gly Val Glu Ala Thr Phe Pro Asp Gly Thr Lys Leu Val Thr Val
                85                  90                  95

Asn Trp Pro Ile Glu Pro Asp Glu His Phe Lys Ala Gly Glu Val Lys
            100                 105                 110
```

```
Phe Gly Cys Asp Lys Asp Ile Glu Leu Asn Ala Gly Lys Glu Val Thr
            115                 120                 125

Glu Leu Glu Val Thr Asn Glu Gly Pro Lys Ser Leu His Val Gly Ser
        130                 135                 140

His Phe His Phe Glu Ala Asn Lys Ala Leu Lys Phe Asp Arg Glu
145                 150                 155                 160

Lys Ala Tyr Gly Lys Arg Leu Asp Ile Pro Ser Gly Asn Thr Leu Arg
                165                 170                 175

Ile Gly Ala Gly Gln Thr Arg Lys Val Gln Leu Ile Pro Leu Gly Gly
            180                 185                 190

Ser Lys Lys Val Ile Gly Met Asn Gly Leu Val Asn Asn Ile Ala Asp
        195                 200                 205

Glu Arg His Lys His Lys Ala Leu Glu Lys Ala Lys Ser His Gly Phe
210                 215                 220

Ile Lys
225

<210> SEQ ID NO 12
<211> LENGTH: 568
<212> TYPE: PRT
<213> ORGANISM: Helicobacter felis

<400> SEQUENCE: 12

Met Lys Met Lys Lys Gln Glu Tyr Val Asn Thr Tyr Gly Pro Thr Thr
1               5                   10                  15

Gly Asp Lys Val Arg Leu Gly Asp Thr Asp Leu Trp Ala Glu Val Glu
            20                  25                  30

His Asp Tyr Thr Thr Tyr Gly Glu Glu Leu Lys Phe Gly Ala Gly Lys
        35                  40                  45

Thr Ile Arg Glu Gly Met Gly Gln Ser Asn Ser Pro Asp Glu Asn Thr
    50                  55                  60

Leu Asp Leu Val Ile Thr Asn Ala Met Ile Ile Asp Tyr Thr Gly Ile
65                  70                  75                  80

Tyr Lys Ala Asp Ile Gly Ile Lys Asn Gly Lys Ile His Gly Ile Gly
                85                  90                  95

Lys Ala Gly Asn Lys Asp Met Gln Asp Gly Val Ser Pro His Met Val
            100                 105                 110

Val Gly Val Gly Thr Glu Ala Leu Ala Gly Glu Gly Met Ile Ile Thr
        115                 120                 125

Ala Gly Gly Ile Asp Ser His Thr His Phe Leu Ser Pro Gln Gln Phe
    130                 135                 140

Pro Thr Ala Leu Ala Asn Gly Val Thr Thr Met Phe Gly Gly Gly Thr
145                 150                 155                 160

Gly Pro Val Asp Gly Thr Asn Ala Thr Thr Ile Thr Pro Gly Lys Trp
                165                 170                 175

Asn Leu His Arg Met Leu Arg Ala Ala Glu Glu Tyr Ser Met Asn Val
            180                 185                 190

Gly Phe Leu Gly Lys Gly Asn Ser Ser Lys Lys Gln Leu Val Glu
        195                 200                 205

Gln Ile Glu Ala Gly Ala Ile Gly Phe Lys Leu His Glu Asp Trp Gly
    210                 215                 220

Thr Thr Pro Ser Ala Ile Asp His Cys Leu Ser Val Ala Asp Glu Tyr
225                 230                 235                 240

Asp Val Gln Val Cys Ile His Thr Asp Thr Val Asn Glu Ala Gly Tyr
```

245                 250                 255
Val Asp Asp Thr Leu Asn Ala Met Asn Gly Arg Ala Ile His Ala Tyr
                260                 265                 270

His Ile Glu Gly Ala Gly Gly His Ser Pro Asp Val Ile Thr Met
        275                 280                 285

Ala Gly Glu Leu Asn Ile Leu Pro Ser Ser Thr Thr Pro Thr Ile Pro
    290                 295                 300

Tyr Thr Ile Asn Thr Val Ala Glu His Leu Asp Met Leu Met Thr Cys
305                 310                 315                 320

His His Leu Asp Lys Arg Ile Arg Glu Asp Leu Gln Phe Ser Gln Ser
                325                 330                 335

Arg Ile Arg Pro Gly Ser Ile Ala Ala Glu Asp Val Leu His Asp Ile
                340                 345                 350

Gly Val Ile Ala Met Thr Ser Ser Asp Ser Gln Ala Met Gly Arg Ala
                355                 360                 365

Gly Glu Val Ile Pro Arg Thr Trp Gln Thr Ala Asp Lys Asn Lys Lys
            370                 375                 380

Glu Phe Gly Lys Leu Pro Glu Asp Ser Ala Asp Asn Asp Asn Phe Arg
385                 390                 395                 400

Ile Lys Arg Tyr Ile Ser Lys Tyr Thr Ile Asn Pro Ala Leu Thr His
                405                 410                 415

Gly Val Ser Glu Tyr Ile Gly Ser Val Glu Glu Gly Lys Ile Ala Asp
                420                 425                 430

Leu Val Val Trp Asn Pro Ala Phe Phe Gly Val Lys Pro Lys Ile Val
            435                 440                 445

Ile Lys Gly Gly Met Val Val Phe Ser Glu Met Gly Asp Ser Asn Ala
    450                 455                 460

Ser Val Pro Thr Pro Gln Pro Val Tyr Tyr Arg Glu Met Phe Gly His
465                 470                 475                 480

His Gly Lys Ala Lys Phe Asp Thr Ser Ile Thr Phe Val Ser Lys Val
                485                 490                 495

Ala Tyr Glu Asn Gly Val Lys Glu Lys Leu Gly Leu Glu Arg Lys Val
                500                 505                 510

Leu Pro Val Lys Asn Cys Arg Asn Ile Thr Lys Lys Asp Phe Lys Phe
            515                 520                 525

Asn Asn Lys Thr Ala His Ile Thr Val Asp Pro Lys Thr Phe Glu Val
    530                 535                 540

Phe Val Asp Gly Lys Leu Cys Thr Ser Lys Pro Ala Ser Glu Val Pro
545                 550                 555                 560

Leu Ala Gln Arg Tyr Thr Phe Phe
                565

<210> SEQ ID NO 13
<211> LENGTH: 2452
<212> TYPE: DNA
<213> ORGANISM: Helicobacter felis
<220> FEATURE:
<221> NAME/KEY: CDS
<222> LOCATION: (48)..(728)
<220> FEATURE:
<221> NAME/KEY: CDS
<222> LOCATION: (739)..(2445)

<400> SEQUENCE: 13
aggactataa tcccattgcc tttaaaattt aacacaagga gtaatag gtg aaa ctc    56
                                                 Val Lys Leu
                                                  1

-continued

| | |
|---|---|
| aca ccc aaa gag caa gaa aag ttc ttg tta tat tat gcg ggc gaa gtg<br>Thr Pro Lys Glu Gln Glu Lys Phe Leu Leu Tyr Tyr Ala Gly Glu Val<br>5                                      10                          15 | 104 |
| gct aga aag cgc aaa gca gag ggc tta aag ctc aac caa ccc gaa gcc<br>Ala Arg Lys Arg Lys Ala Glu Gly Leu Lys Leu Asn Gln Pro Glu Ala<br>20                        25                     30                     35 | 152 |
| att gcc tac att agt gcc cat att atg gac gag gcg cgt cgt ggc aaa<br>Ile Ala Tyr Ile Ser Ala His Ile Met Asp Glu Ala Arg Arg Gly Lys<br>               40                     45                      50 | 200 |
| aaa acc gtt gcg gaa ctt atg gaa gag tgt atg cac ttt ttg aaa aaa<br>Lys Thr Val Ala Glu Leu Met Glu Glu Cys Met His Phe Leu Lys Lys<br>        55                          60                        65 | 248 |
| gac gag gtg atg ccc ggg gtg ggg aat atg gtc cct gat ttg ggc gtg<br>Asp Glu Val Met Pro Gly Val Gly Asn Met Val Pro Asp Leu Gly Val<br>             70                          75                       80 | 296 |
| gaa gcc act ttc ccc gat ggc acc aaa ctc gta act gtg aat tgg ccc<br>Glu Ala Thr Phe Pro Asp Gly Thr Lys Leu Val Thr Val Asn Trp Pro<br>85                                90                     95 | 344 |
| atc gaa cct gat gaa cac ttt aag gcg ggt gaa gtg aaa ttt ggc tgt<br>Ile Glu Pro Asp Glu His Phe Lys Ala Gly Glu Val Lys Phe Gly Cys<br>100                         105                   110              115 | 392 |
| gat aaa gac att gaa ctc aac gca ggt aag gaa gtt acc gaa cta gaa<br>Asp Lys Asp Ile Glu Leu Asn Ala Gly Lys Glu Val Thr Glu Leu Glu<br>                   120                   125                  130 | 440 |
| gtt act aac gaa gga cct aaa tcc ttg cat gtg ggt agc cat ttc cac<br>Val Thr Asn Glu Gly Pro Lys Ser Leu His Val Gly Ser His Phe His<br>            135                   140                   145 | 488 |
| ttc ttt gaa gcc aac aaa gca ttg aaa ttc gat cgg gaa aaa gcc tat<br>Phe Phe Glu Ala Asn Lys Ala Leu Lys Phe Asp Arg Glu Lys Ala Tyr<br>150                       155                   160 | 536 |
| ggc aaa cgc cta gat att ccc tct ggc aac aca cta cgc att ggg gca<br>Gly Lys Arg Leu Asp Ile Pro Ser Gly Asn Thr Leu Arg Ile Gly Ala<br>165                       170                   175 | 584 |
| gga caa acc cgt aaa gtg cag tta atc cct ctt ggc ggt agt aaa aaa<br>Gly Gln Thr Arg Lys Val Gln Leu Ile Pro Leu Gly Gly Ser Lys Lys<br>180                       185                   190              195 | 632 |
| gtg att ggc atg aac ggg ctt gtg aat aat att gcg gac gaa cgc cat<br>Val Ile Gly Met Asn Gly Leu Val Asn Asn Ile Ala Asp Glu Arg His<br>                   200                   205                  210 | 680 |
| aaa cac aaa gcg cta gac aaa gca aaa tct cac gga ttt atc aag taa<br>Lys His Lys Ala Leu Asp Lys Ala Lys Ser His Gly Phe Ile Lys<br>            215                   220                   225 | 728 |
| ggagactccc atg aaa atg aaa aaa caa gag tat gta aat acc tac gga<br>                 Met Lys Met Lys Lys Gln Glu Tyr Val Asn Thr Tyr Gly<br>                            230                            235                   240 | 777 |
| ccc acc aca ggc gat aaa gtg cgc tta gga gat acc gat ctt tgg gca<br>Pro Thr Thr Gly Asp Lys Val Arg Leu Gly Asp Thr Asp Leu Trp Ala<br>                   245                   250                  255 | 825 |
| gaa gta gaa cat gac tat acc acc tat ggc gaa gaa ctc aaa ttc ggt<br>Glu Val Glu His Asp Tyr Thr Thr Tyr Gly Glu Glu Leu Lys Phe Gly<br>            260                   265                   270 | 873 |
| gca ggt aaa act atc cgt gag ggt atg ggt cag agc aat agc cca gat<br>Ala Gly Lys Thr Ile Arg Glu Gly Met Gly Gln Ser Asn Ser Pro Asp<br>275                       280                   285 | 921 |
| gaa aac acc tta gat tta gtg atc acc aac gcg atg att att gac tac<br>Glu Asn Thr Leu Asp Leu Val Ile Thr Asn Ala Met Ile Ile Asp Tyr<br>          290                   295                   300 | 969 |
| acc ggg att tac aaa gcc gac att ggc att aaa aat ggc aaa atc cat<br>Thr Gly Ile Tyr Lys Ala Asp Ile Gly Ile Lys Asn Gly Lys Ile His | 1017 |

```
                305                 310                 315                 320
ggc att ggc aag gca gga aac aag gac atg caa gat ggc gta agc cct         1065
Gly Ile Gly Lys Ala Gly Asn Lys Asp Met Gln Asp Gly Val Ser Pro
                    325                 330                 335 cat atg gtc gtg ggt gtg ggc aca gaa gca cta gca ggg gaa ggt atg         1113
His Met Val Val Gly Val Gly Thr Glu Ala Leu Ala Gly Glu Gly Met
                340                 345                 350 att att acc gct ggg ggg atc gat tca cac acc cac ttc ctc tct cca         1161
Ile Ile Thr Ala Gly Gly Ile Asp Ser His Thr His Phe Leu Ser Pro
            355                 360                 365 caa caa ttc cct acc gct cta gcc aat ggc gtt aca aca atg ttt ggc         1209
Gln Gln Phe Pro Thr Ala Leu Ala Asn Gly Val Thr Thr Met Phe Gly
        370                 375                 380 ggt gga aca ggc ccc gta gat ggc acg aat gcg act acc atc act ccg         1257
Gly Gly Thr Gly Pro Val Asp Gly Thr Asn Ala Thr Thr Ile Thr Pro
385                 390                 395                 400 ggc aaa tgg aac ttg cac cgc atg ttg cgc gca gca gaa gag tat tct         1305
Gly Lys Trp Asn Leu His Arg Met Leu Arg Ala Ala Glu Glu Tyr Ser
                    405                 410                 415 atg aat gtg ggc ttt ttg ggc aaa ggc aat agc tct agt aaa aaa caa         1353
Met Asn Val Gly Phe Leu Gly Lys Gly Asn Ser Ser Ser Lys Lys Gln
                420                 425                 430 ctt gta gaa caa gta gaa gcg ggc gcg att ggt ttt aaa ttg cat gaa         1401
Leu Val Glu Gln Val Glu Ala Gly Ala Ile Gly Phe Lys Leu His Glu
            435                 440                 445 gac tgg ggc aca act cca agt gcg atc gat cac tgc ttg agc gta gca         1449
Asp Trp Gly Thr Thr Pro Ser Ala Ile Asp His Cys Leu Ser Val Ala
        450                 455                 460 gat gaa tac gat gtg caa gtt tgt ata cac acc gat acg gtc aat gag         1497
Asp Glu Tyr Asp Val Gln Val Cys Ile His Thr Asp Thr Val Asn Glu
465                 470                 475                 480 gca ggt tat gta gat gac acc cta aat gca atg aac ggg cgc gcc atc         1545
Ala Gly Tyr Val Asp Asp Thr Leu Asn Ala Met Asn Gly Arg Ala Ile
                    485                 490                 495 cat gcc tac cac att gag gga gcg ggt gga gga cac tca cct gat gtt         1593
His Ala Tyr His Ile Glu Gly Ala Gly Gly Gly His Ser Pro Asp Val
                500                 505                 510 atc acc atg gca ggc gaa gtg aat att cta ccc tcc tcc aca acc cct         1641
Ile Thr Met Ala Gly Glu Val Asn Ile Leu Pro Ser Ser Thr Thr Pro
            515                 520                 525 act atc ccc tat acc att aat acg gtt gca gaa cac tta gac atg ctt         1689
Thr Ile Pro Tyr Thr Ile Asn Thr Val Ala Glu His Leu Asp Met Leu
        530                 535                 540 atg acc tgc cac cac cta gat aaa cgc atc cgc gag gat ctc caa ttt         1737
Met Thr Cys His His Leu Asp Lys Arg Ile Arg Glu Asp Leu Gln Phe
545                 550                 555                 560 tct caa agc cgt atc cgc ccc ggc tct atc gcc gct gaa gat gtg ctc         1785
Ser Gln Ser Arg Ile Arg Pro Gly Ser Ile Ala Ala Glu Asp Val Leu
                    565                 570                 575 cat gat atc ggt gtg atc gcg atg aca agt tcc gat tcg caa gca atg         1833
His Asp Ile Gly Val Ile Ala Met Thr Ser Ser Asp Ser Gln Ala Met
                580                 585                 590 ggg cgc gct ggg gaa gtg att cct aga act tgg caa act gca gac aag         1881
Gly Arg Ala Gly Glu Val Ile Pro Arg Thr Trp Gln Thr Ala Asp Lys
            595                 600                 605 aat aaa aaa gaa ttt ggt aag ctt cct gaa gat ggt gca gat aat gac         1929
Asn Lys Lys Glu Phe Gly Lys Leu Pro Glu Asp Gly Ala Asp Asn Asp
        610                 615                 620 aac ttc cgc atc aaa cgc tat atc tcc aaa tac acc att aat ccc gct         1977
```

-continued

```
Asn Phe Arg Ile Lys Arg Tyr Ile Ser Lys Tyr Thr Ile Asn Pro Ala
625                 630                 635                 640 ttg acc cat ggc gtg agc gag tat atc ggc tct gtg gaa gag ggc aag    2025
Leu Thr His Gly Val Ser Glu Tyr Ile Gly Ser Val Glu Glu Gly Lys
                    645                 650                 655 atc gcc gac ttg gtg gtg tgg aat cct gcc ttt ttt ggc gta aaa ccc    2073
Ile Ala Asp Leu Val Val Trp Asn Pro Ala Phe Phe Gly Val Lys Pro
                660                 665                 670 aaa atc gtg atc aaa ggc ggt atg gtg gtg ttc tct gaa atg ggc gat    2121
Lys Ile Val Ile Lys Gly Gly Met Val Val Phe Ser Glu Met Gly Asp
            675                 680                 685 tct aat gcg tct gtg ccc act cct cag ccg gtt tat tac cgc gaa atg    2169
Ser Asn Ala Ser Val Pro Thr Pro Gln Pro Val Tyr Tyr Arg Glu Met
690                 695                 700 ttt ggg cat cac ggc aag gcg aaa ttt gac acc agc atc act ttt gtt    2217
Phe Gly His His Gly Lys Ala Lys Phe Asp Thr Ser Ile Thr Phe Val
705                 710                 715                 720 tcc aaa gtc gcc tat gaa aat ggt gtg aaa gaa aaa cta ggt tta gag    2265
Ser Lys Val Ala Tyr Glu Asn Gly Val Lys Glu Lys Leu Gly Leu Glu
                    725                 730                 735 cgc aag gtg ctc ccc gtg aaa aac tgc cgt aac atc acc aag aag gac    2313
Arg Lys Val Leu Pro Val Lys Asn Cys Arg Asn Ile Thr Lys Lys Asp
                740                 745                 750 ttc aag ttc aac gac aaa act gca aaa atc acc gtc gat ccg aaa acc    2361
Phe Lys Phe Asn Asp Lys Thr Ala Lys Ile Thr Val Asp Pro Lys Thr
            755                 760                 765 ttc gag gtc ttt gta gat ggc aaa ctc tgc acc tct aaa ccc acc tct    2409
Phe Glu Val Phe Val Asp Gly Lys Leu Cys Thr Ser Lys Pro Thr Ser
770                 775                 780 gaa gtg cct cta gcc caa cgc tac act ttc ttc tag gcataat             2452
Glu Val Pro Leu Ala Gln Arg Tyr Thr Phe Phe
785                 790                 795

<210> SEQ ID NO 14
<211> LENGTH: 226
<212> TYPE: PRT
<213> ORGANISM: Helicobacter felis

<400> SEQUENCE: 14

Val Lys Leu Thr Pro Lys Glu Gln Glu Lys Phe Leu Leu Tyr Tyr Ala
1               5                   10                  15

Gly Glu Val Ala Arg Lys Arg Lys Ala Glu Gly Leu Lys Leu Asn Gln
                20                  25                  30

Pro Glu Ala Ile Ala Tyr Ile Ser Ala His Ile Met Asp Glu Ala Arg
            35                  40                  45

Arg Gly Lys Lys Thr Val Ala Glu Leu Met Glu Glu Cys Met His Phe
        50                  55                  60

Leu Lys Lys Asp Glu Val Met Pro Gly Val Gly Asn Met Val Pro Asp
65                  70                  75                  80

Leu Gly Val Glu Ala Thr Phe Pro Asp Gly Thr Lys Leu Val Thr Val
                85                  90                  95

Asn Trp Pro Ile Glu Pro Asp Glu His Phe Lys Ala Gly Glu Val Lys
            100                 105                 110

Phe Gly Cys Asp Lys Asp Ile Glu Leu Asn Ala Gly Lys Glu Val Thr
        115                 120                 125

Glu Leu Glu Val Thr Asn Glu Gly Pro Lys Ser Leu His Val Gly Ser
    130                 135                 140

His Phe His Phe Phe Glu Ala Asn Lys Ala Leu Lys Phe Asp Arg Glu
```

```
                145                 150                 155                 160
Lys Ala Tyr Gly Lys Arg Leu Asp Ile Pro Ser Gly Asn Thr Leu Arg
                    165                 170                 175

Ile Gly Ala Gly Gln Thr Arg Lys Val Gln Leu Ile Pro Leu Gly Gly
                    180                 185                 190

Ser Lys Lys Val Ile Gly Met Asn Gly Leu Val Asn Asn Ile Ala Asp
                    195                 200                 205

Glu Arg His Lys His Lys Ala Leu Asp Lys Ala Lys Ser His Gly Phe
                    210                 215                 220

Ile Lys
225

<210> SEQ ID NO 15
<211> LENGTH: 568
<212> TYPE: PRT
<213> ORGANISM: Helicobacter felis

<400> SEQUENCE: 15

Met Lys Met Lys Lys Gln Glu Tyr Val Asn Thr Tyr Gly Pro Thr Thr
  1               5                  10                  15

Gly Asp Lys Val Arg Leu Gly Asp Thr Asp Leu Trp Ala Glu Val Glu
                 20                  25                  30

His Asp Tyr Thr Thr Tyr Gly Glu Glu Leu Lys Phe Gly Ala Gly Lys
             35                  40                  45

Thr Ile Arg Glu Gly Met Gly Gln Ser Asn Ser Pro Asp Glu Asn Thr
         50                  55                  60

Leu Asp Leu Val Ile Thr Asn Ala Met Ile Ile Asp Tyr Thr Gly Ile
 65                  70                  75                  80

Tyr Lys Ala Asp Ile Gly Ile Lys Asn Gly Lys Ile His Gly Ile Gly
                 85                  90                  95

Lys Ala Gly Asn Lys Asp Met Gln Asp Gly Val Ser Pro His Met Val
            100                 105                 110

Val Gly Val Gly Thr Glu Ala Leu Ala Gly Glu Gly Met Ile Ile Thr
        115                 120                 125

Ala Gly Gly Ile Asp Ser His Thr His Phe Leu Ser Pro Gln Gln Phe
    130                 135                 140

Pro Thr Ala Leu Ala Asn Gly Val Thr Thr Met Phe Gly Gly Gly Thr
145                 150                 155                 160

Gly Pro Val Asp Gly Thr Asn Ala Thr Thr Ile Thr Pro Gly Lys Trp
                165                 170                 175

Asn Leu His Arg Met Leu Arg Ala Ala Glu Glu Tyr Ser Met Asn Val
            180                 185                 190

Gly Phe Leu Gly Lys Gly Asn Ser Ser Lys Lys Gln Leu Val Glu
        195                 200                 205

Gln Val Glu Ala Gly Ala Ile Gly Phe Lys Leu His Glu Asp Trp Gly
    210                 215                 220

Thr Thr Pro Ser Ala Ile Asp His Cys Leu Ser Val Ala Asp Glu Tyr
225                 230                 235                 240

Asp Val Gln Val Cys Ile His Thr Asp Thr Val Asn Glu Ala Gly Tyr
                245                 250                 255

Val Asp Asp Thr Leu Asn Ala Met Asn Gly Arg Ala Ile His Ala Tyr
            260                 265                 270

His Ile Glu Gly Ala Gly Gly Gly His Ser Pro Asp Val Ile Thr Met
        275                 280                 285
```

```
Ala Gly Glu Val Asn Ile Leu Pro Ser Ser Thr Thr Pro Thr Ile Pro
    290                 295                 300
Tyr Thr Ile Asn Thr Val Ala Glu His Leu Asp Met Leu Met Thr Cys
305                 310                 315                 320
His His Leu Asp Lys Arg Ile Arg Glu Asp Leu Gln Phe Ser Gln Ser
                325                 330                 335
Arg Ile Arg Pro Gly Ser Ile Ala Ala Glu Asp Val Leu His Asp Ile
            340                 345                 350
Gly Val Ile Ala Met Thr Ser Ser Asp Ser Gln Ala Met Gly Arg Ala
        355                 360                 365
Gly Glu Val Ile Pro Arg Thr Trp Gln Thr Ala Asp Lys Asn Lys Lys
    370                 375                 380
Glu Phe Gly Lys Leu Pro Glu Asp Gly Ala Asp Asn Asp Asn Phe Arg
385                 390                 395                 400
Ile Lys Arg Tyr Ile Ser Lys Tyr Thr Ile Asn Pro Ala Leu Thr His
                405                 410                 415
Gly Val Ser Glu Tyr Ile Gly Ser Val Glu Glu Gly Lys Ile Ala Asp
            420                 425                 430
Leu Val Val Trp Asn Pro Ala Phe Phe Gly Val Lys Pro Lys Ile Val
        435                 440                 445
Ile Lys Gly Gly Met Val Val Phe Ser Glu Met Gly Asp Ser Asn Ala
    450                 455                 460
Ser Val Pro Thr Pro Gln Pro Val Tyr Tyr Arg Glu Met Phe Gly His
465                 470                 475                 480
His Gly Lys Ala Lys Phe Asp Thr Ser Ile Thr Phe Val Ser Lys Val
                485                 490                 495
Ala Tyr Glu Asn Gly Val Lys Glu Lys Leu Gly Leu Glu Arg Lys Val
            500                 505                 510
Leu Pro Val Lys Asn Cys Arg Asn Ile Thr Lys Lys Asp Phe Lys Phe
        515                 520                 525
Asn Asp Lys Thr Ala Lys Ile Thr Val Asp Pro Lys Thr Phe Glu Val
    530                 535                 540
Phe Val Asp Gly Lys Leu Cys Thr Ser Lys Pro Thr Ser Glu Val Pro
545                 550                 555                 560
Leu Ala Gln Arg Tyr Thr Phe Phe
                565

<210> SEQ ID NO 16
<211> LENGTH: 21
<212> TYPE: DNA
<213> ORGANISM: Helicobacter felis

<400> SEQUENCE: 16
catgcacttt tgaaaaaag a                                            21

<210> SEQ ID NO 17
<211> LENGTH: 16
<212> TYPE: DNA
<213> ORGANISM: Helicobacter felis

<400> SEQUENCE: 17
tatggtggtc ttctct                                                 16

<210> SEQ ID NO 18
<211> LENGTH: 32
<212> TYPE: DNA
<213> ORGANISM: Helicobacter felis
```

```
<400> SEQUENCE: 18
ggagtaacat atgaaactca cacccaaaga gc                           32

<210> SEQ ID NO 19
<211> LENGTH: 27
<212> TYPE: DNA
<213> ORGANISM: Helicobacter felis

<400> SEQUENCE: 19
cacacccacg accatgtgag ggcttac                                 27

<210> SEQ ID NO 20
<211> LENGTH: 27
<212> TYPE: DNA
<213> ORGANISM: Helicobacter felis

<400> SEQUENCE: 20
gtaagccctc acatggtcgt gggtgtg                                 27

<210> SEQ ID NO 21
<211> LENGTH: 34
<212> TYPE: DNA
<213> ORGANISM: Helicobacter felis

<400> SEQUENCE: 21
cgaattcgga tcctagaaga aagtgtagcg ctgg                         34
```

HELICOBACTER FELIS VACCINE

FIELD OF THE INVENTION

The present invention relates to novel *Helicobacter* urease subunit polypeptides, nucleic acid sequences encoding these polypeptides, to the polypeptides for use in vaccines and to the use in the manufacturing thereof, to vaccines comprising said polypeptides and to methods for the preparation of such vaccines. Further, the invention relates to diagnostic methods for the detection of the nucleic acid sequences, the polypeptides and antibodies against the polypeptides.

BACKGROUND OF THE INVENTION

Several *Helicobacter* species are the cause of pathogenesis of the gastric epithelium. *Helicobacter pylori*, and to a lesser extent *H. heilmannii* are known to cause gastritis, a major factor in the development of peptic ulcers and gastric lymphoma in humans. *Helicobacter felis* is most likely the cause of gastric infections in both cats and dogs. In order to survive the highly acidic environment of the stomach, members of the *Helicobacter* family produce a urease that is capable of hydrolysing the urea present in gastric juice. This hydrolysation sets free an amount of NH$_4$OH that suffices to neutralise the environment of the bacterium. It is known that the urease plays a role in the colonization of the bacterium as well as in its pathogenesis.

Genes encoding urease have been described and sequenced for both *Helicobacter pylori* (Labigne et al., J. Bacteriol. 173: 1920-1931 (1991)) and *Helicobacter felis* (Ferrero et al., Molec. Microbiol. 9, 323-333 (1993)). Of the seven genes involved in urease expression and secretion, only two genes encode the two structural subunits urease A and B of the urease enzyme, ureA and ureB. These two polypeptides form a polypeptide complex having urease activity.

Vaccines against infections caused by both *H. pylori* and *felis* have been made and have been the subject of i.a. International Patent Applications WO 94/09823 and WO 96/34624. Several attempt have been made to use *H. pylori* urease as a vaccine component for the protection of cats against *H. felis* infection. Although indeed a certain level of protection can be obtained, the results are far from the 100% protection that would be desirable. From animal experiments published so far, it becomes clear that a significant number of animals vaccinated with *H. pylori* is not at all protected against subsequent challenge with *H. felis*. Protection of cats vaccinated with purified urease from either *H. felis* or *pylori* has not been described. Vaccinating cats with *H. felis* whole cell lysates might theoretically be feasible but is not a practical option. This is because in spite of many attempts for improvement, *H. felis* is difficult to grow.

There clearly is a need for an efficacious vaccine, based upon homologous components, and it is clear that the known *H. felis* urease does not confer full protection.

SUMMARY OF THE INVENTION

It is an object of the present invention to provide a *H. felis* urease which is able to induce protection against *Helicobacter felis* infection in dogs and cats. It was surprisingly found that in *H. felis* a second urease exists, of which the genes encoding the structural subunits share only low homology with the known *H. felis* ureA and B genes. The novel urease is named ureaseXY, in order to discriminate it from the known urease AB. The newly found urease has been discovered in *H. felis*, and is not present in *H. pylori*.

BRIEF SUMMARY OF THE DRAWINGS

Figure 1A:
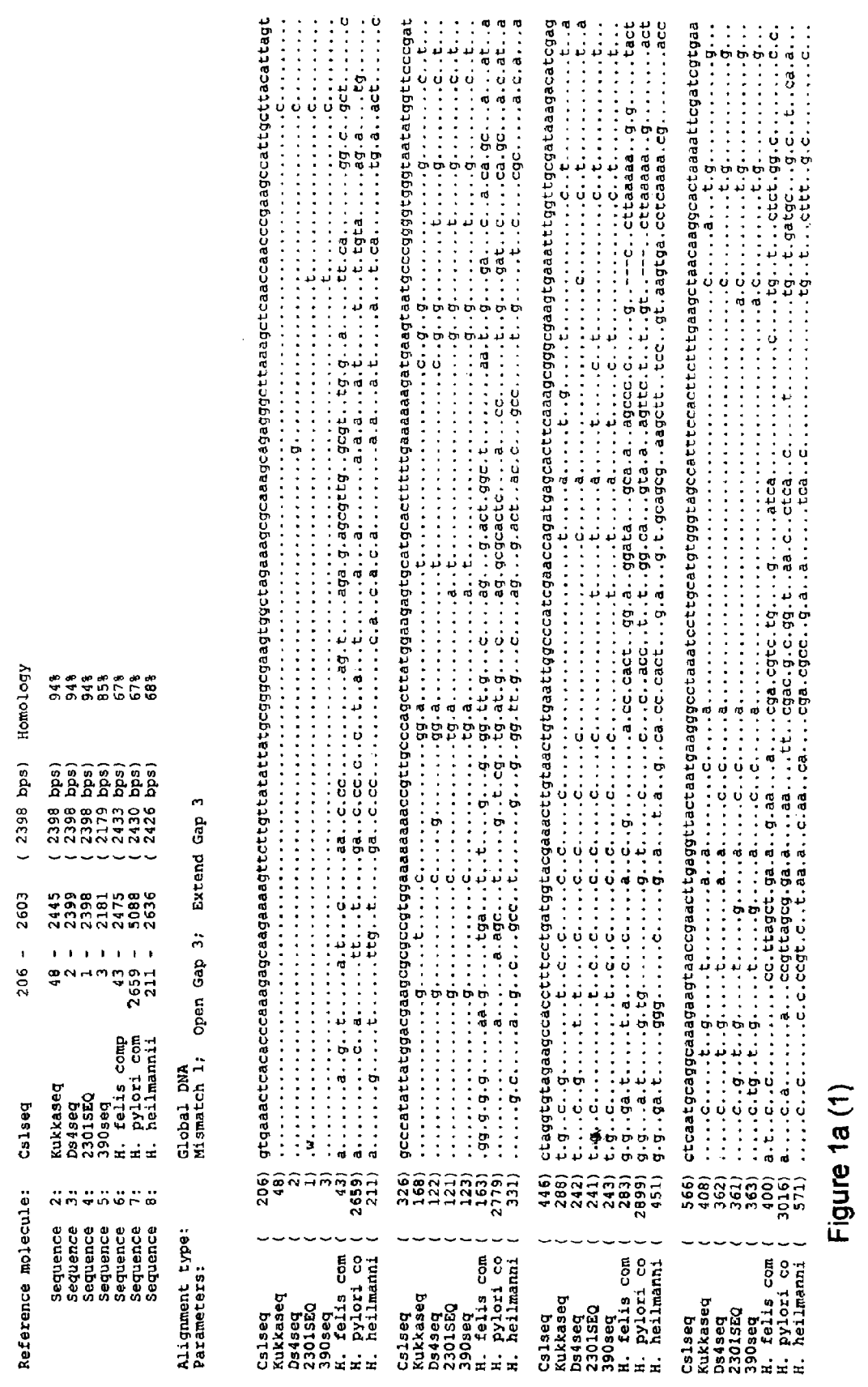
Figure 1A:
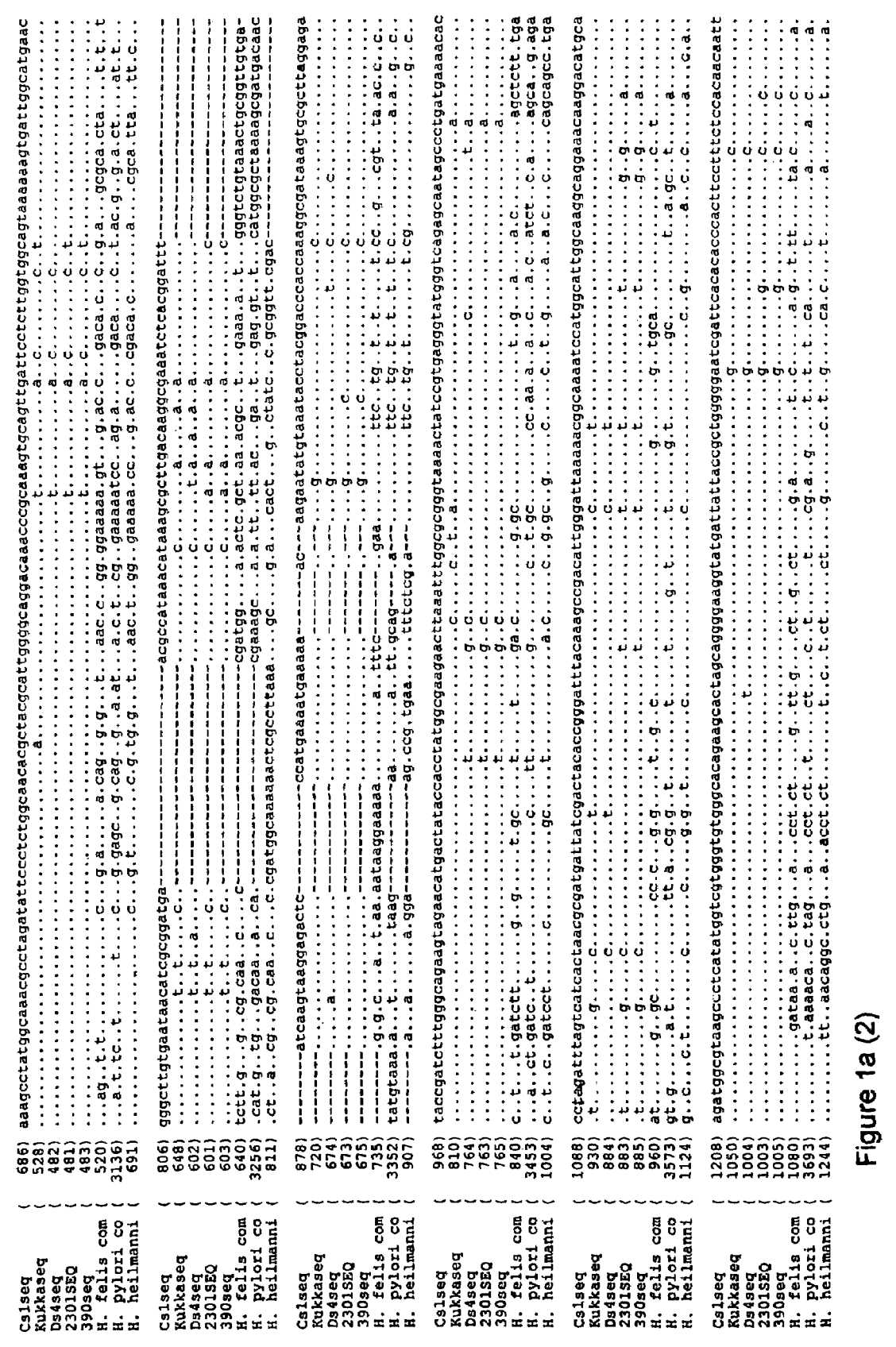
Figure 1A:
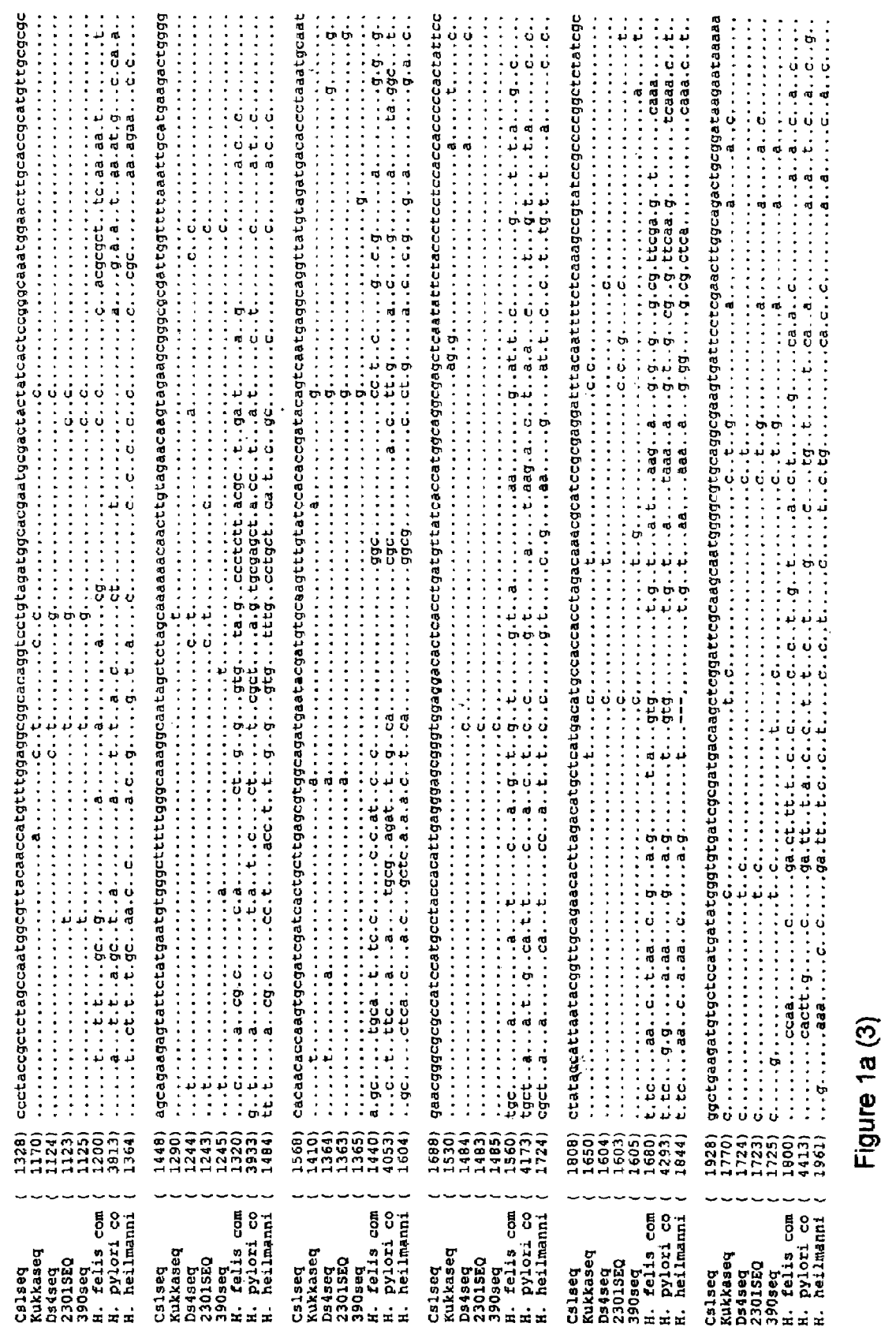
Figure 1A:
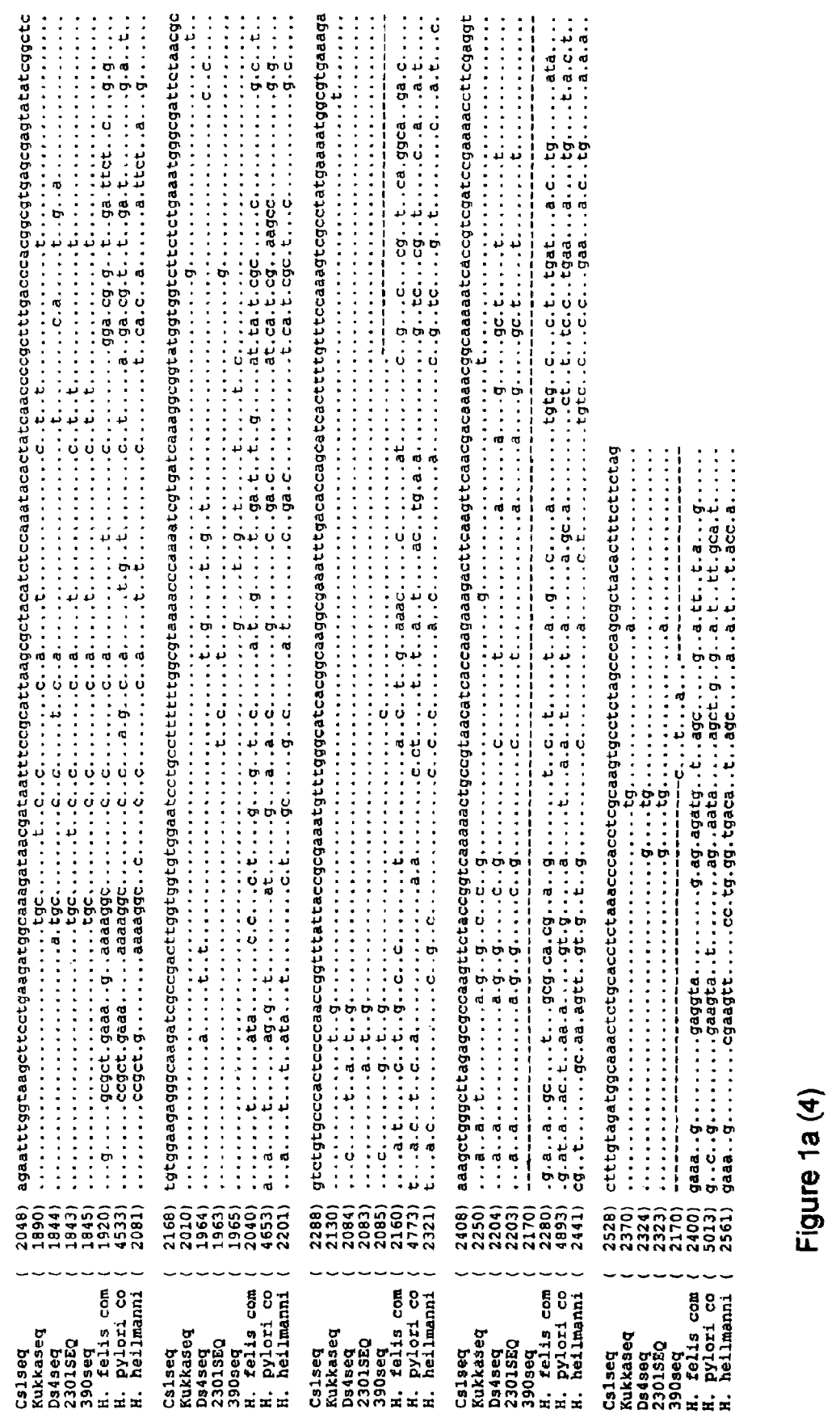

FIG. 1a: Comparison of the nucleic acid sequence encoding UreX and Y, including a short non-coding region bridging the two coding sequences, from *Helicobacter felis* species CS1, SEQ ID NO: 1; Kukka, SEQ ID NO: 13; Ds4, SEQ ID NO: 10; 2301, SEQ ID NO: 4; and 390, SEQ ID NO: 7, with the nucleic acid sequence encoding UreA and B, including a short non-coding region bridging the two encoding sequences, from *Helicobacter felis, pylori*, and *heilmannii*.

FIG. 1b: Comparison of the amino acid sequence of UreX from *Helicobacter felis* species CS1, SEQ ID NO: 2; Kukka, SEQ ID NO: 14; Ds4, SEQ ID NO: 11; 2301, SEQ ID NO: 5; and 390, SEQ ID NO: 8, with the amino acid sequences of UreA from *Helicobacter felis, pylori*, and *heilmannii*.

FIG. 1c: Comparison of the amino acid sequence of UreY from *Helicobacter felis* species CS1, SEQ ID NO: 3; Kukka, SEQ ID NO: 15; Ds4, SEQ ID NO: 12; 2301, SEQ ID NO: 6; and 390, SEQ ID NO: 9, with the amino acid sequences of UreB from *Helicobacter felis, pylori*, and *heilmannii*.

Figure 2:
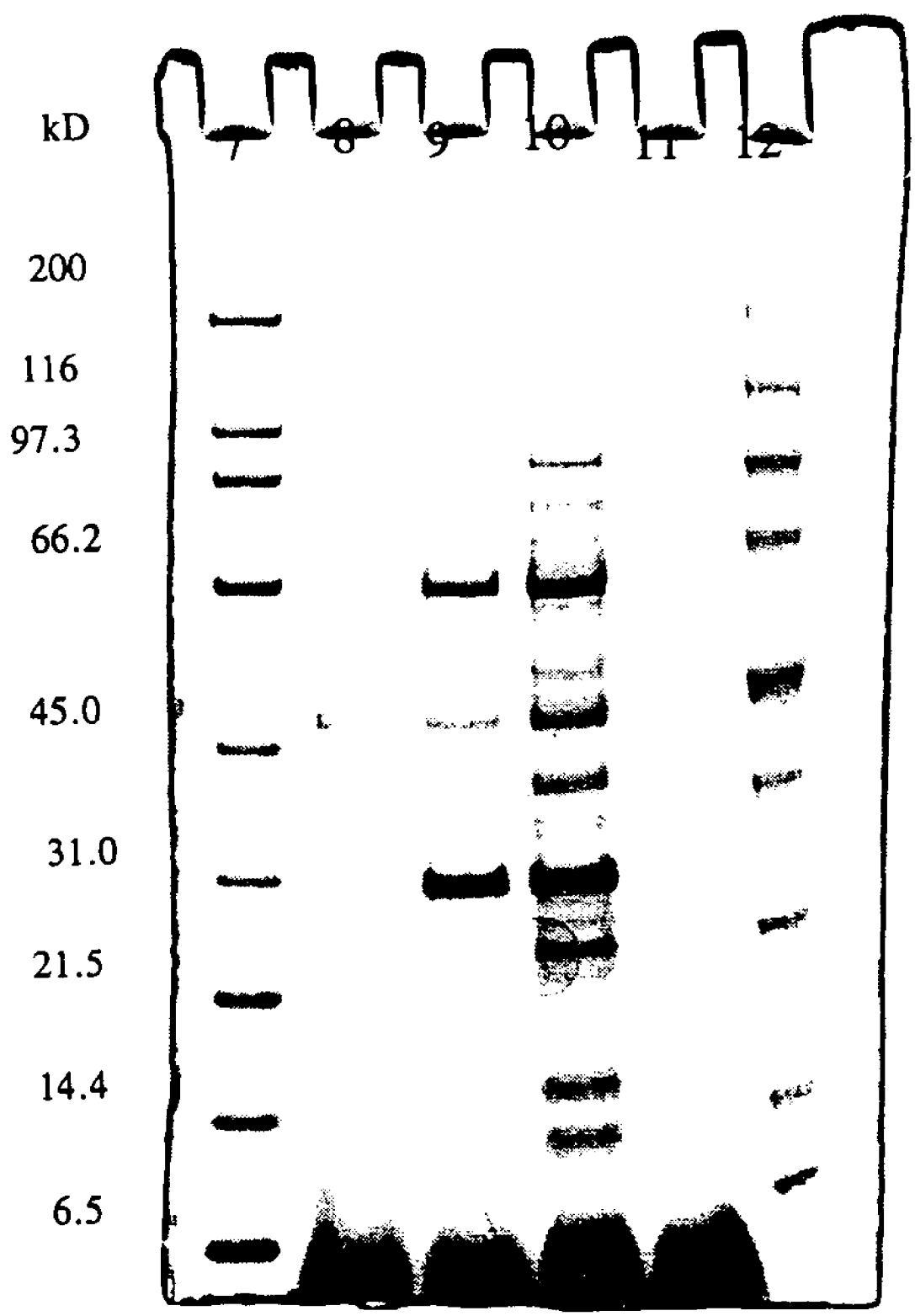
FIG. 2: Polyacrylamide gel of the expression products UreX and UreY

Lane 7: Biorad broad range marker
Lane 8: Complete cell culture before induction (small scale culture)
Lane 9: Complete cell culture after induction (small scale culture)
Lane 10: Complete cell culture after induction (large scale culture)
Lane 11: Supernatant after induction (large scale culture).
Lane 12: Biorad pre-stained marker

DETAILED DESCRIPTION OF THE INVENTION

The overall genetic structure of the genes encoding the two structural urease subunits, UreX and UreY, is comparable to that of the known UreA and B in *H. felis* and *H. pylori*. The sequence homology is however surprisingly low. It was even more surprisingly found that the homology between the ureA and B genes and the novel ureX and Y genes in one single *H. felis* strain is even strikingly lower than the homology between the various ureA and B genes from the various *Helicobacter* species.

Tables 1a, 1b and 1c show the comparison of the ureX and Y genes and the polypeptides they encode from five different *Helicobacter felis* species, with the ureA and B genes and polypeptides from *Helicobacter felis, pylori* and *heilmannii*.

The level of homology of the genes encoding the novel structural urease subunits X and Y and the polypeptides they encode, as compared to that of known ureA and B genes and polypeptide subunits, is presented in Tables 1a, b and c.

TABLE 1a amino acid and nucleic acid homology between the
*H. felis* ureX and various ureA subunits.

| Reference molecule: *H. felis* ureX CS1 | a.a. | n.a. |
| --- | --- | --- |
| *H. felis* ureA | 50% | 57% |
| *H. pylori* ureA | 52% | 60% |
| *H. heilmannii* ureA | 54% | 62% |
| *H. felis* strain Kukka ureX | 100% | 91% |
| *H. felis* strain Ds4 ureX | 99% | 91% |
| *H. felis* strain 2301 ureX | 99% | 91% |
| *H felis* strain 390 ureX | 99% | 91% |

TABLE 1b amino acid and nucleic acid homology between the
H. felis ureY and various ureB subunits.

| Reference molecule: H. felis ureY CS1 | a.a. | n.a. |
|---|---|---|
| H. felis ureB | 73% | 71% |
| H. pylori ureB | 73% | 70% |
| H. heilmannii ureB | 74% | 71% |
| H. felis strain Kukka ureY | 99% | 95% |
| H. felis strain Ds4 ureY | 98% | 94% |
| H. felis strain 2301 ureY | 99% | 95% |

TABLE 1c nucleic acid homology between H. felis ureXY and
various ureAB genes.

| Reference molecule: H. felis ureXY CSI | n.a. |
|---|---|
| H. felis ureAB | 67% |
| H. pylori ureAB | 67% |
| H. heilmannii ureAB | 68% |
| H felis strain Kukka ureXY | 94% |
| H. felis strain Ds4 ureXY | 94% |
| H. felis strain 2301 ureXY | 94% |

One embodiment of the invention thus relates to nucleic acid sequences encoding the novel urease X and Y subunits.

First of all, this embodiment of the invention relates to nucleic acid sequences encoding two subunits of a urease complex such as expressed by *Helicobacter felis*, which have at least 85% homology with SEQ ID NO: 1, or parts thereof with a length of at least 40, preferably 45, more preferably 50 nucleotides encoding at least an immunogenic fragment of one of the subunits. Still even longer fragments, with a length of at least 55, 60 or 70 nucleotides are in that order even more preferred.

A preferred form of this embodiment relates to nucleic acid sequences that encode the urease X subunit polypeptide or the urease Y subunit polypeptide and that have at least 85% homology with SEQ ID NO: 1, or parts thereof with a length of at least 40, preferably 45, more preferably 50 nucleotides encoding at least an immunogenic fragment of the urease X subunit polypeptide or the urease Y subunit polypeptide. Merely as an example: the nucleic acid sequence encoding the urease X subunit of *Helicobacter felis* strain CS1 starts at position 206/207/208 (GTG) (See FIG. 1*a* (1)) and stops at position 884/885/886 (TAA). The nucleic acid sequence encoding the urease Y subunit of *Helicobacter felis* strain CS1 starts at position 897/898/899 (ATG) and stops at position 2601/2602/2603 (TAG).

Still even longer fragments, with a length of at least 55, 60 or 70 nucleotides are in that order even more preferred.

A more preferred form of this embodiment relates to nucleic acid sequences having at least 90%, preferably 94%, and more preferably 97% homology with SEQ ID NO: 1.

Figure 1C:
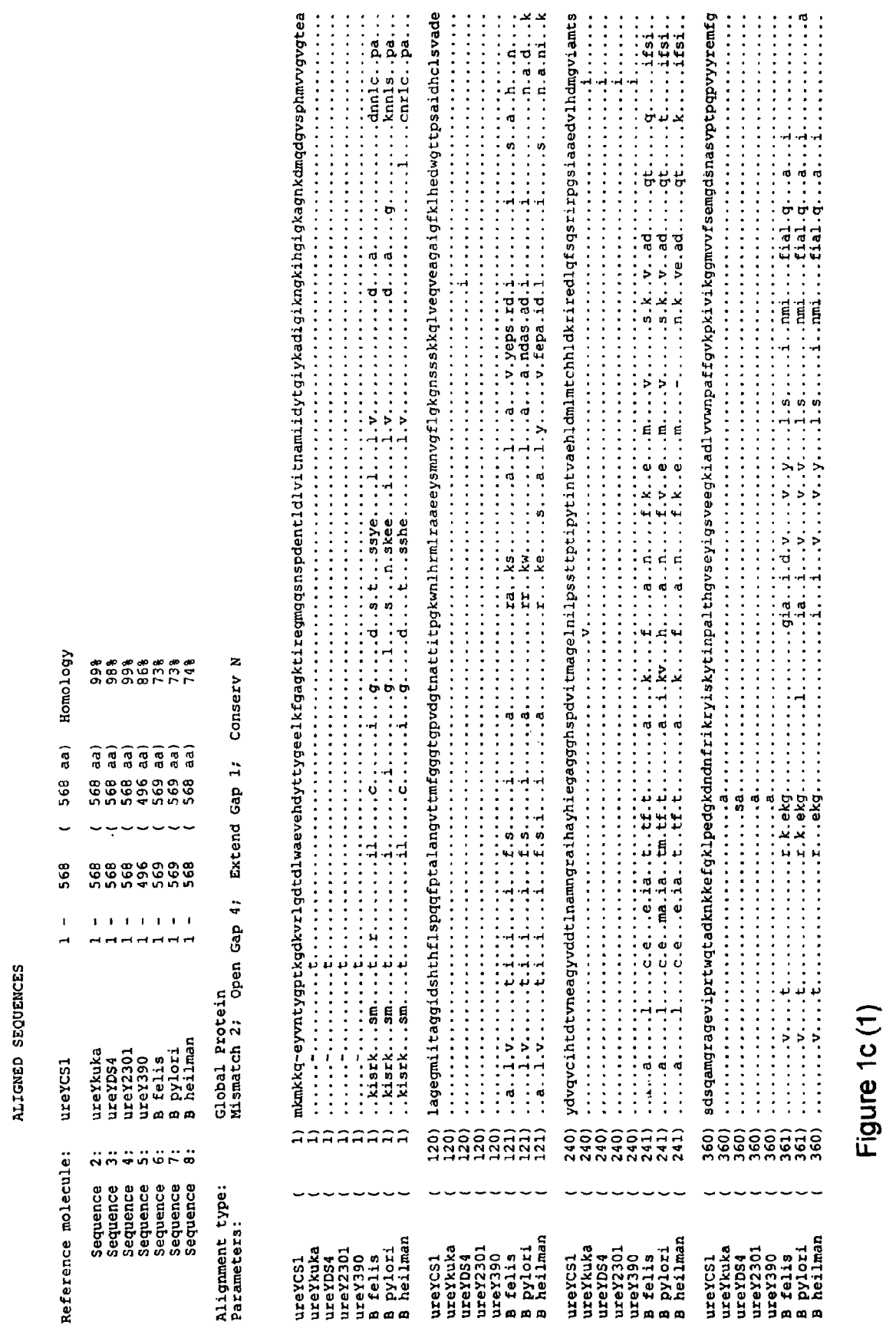

The determination of the homology percentages was done with the computer program Align Plus for Windows, available from Scientific and Educational Software, P.O. Box 72045 Durham, N.C. 27722-2045, USA. Settings used for the nucleic acid comparisons are indicated in FIGS. 1*a*, 1*b* and 1*c*.

Since the present invention discloses nucleic acid sequences encoding novel structural *Helicobacter felis* urease subunits, it is now for the first time possible to obtain such polypeptides in sufficient quantities. This can e.g. be done by using expression systems to express the genes encoding the UreX and UreY subunits. Therefore, in a more preferred embodiment, the invention relates to DNA fragments comprising a nucleic acid sequence according to the invention. Such DNA fragments can e.g. be plasmids, into which a nucleic acid sequence according to the invention is cloned. Such DNA fragments are useful e.g. for enhancing the amount of DNA for use as a probe, as described below.

An essential requirement for the expression of the nucleic acid sequence is an adequate promoter operably linked to the nucleic acid sequence. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment or a nucleic acid sequence according to the invention that is placed under the control of a functionally linked promotor. This can be obtained by means of e.g. standard molecular biology techniques. (Maniatis/Sambrook (Sambrook, J. Molecular cloning: a laboratory manual, 1989. ISBN 0-87969-309-6).

Functionally linked promoters are promotors that are capable of controlling the transcription of the nucleic acid sequences to which they are linked. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 46774688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include the SV40 promoter (Berman, P. W. et al., Science, 222, 524-527, 1983) or the metallothionein promoter (Brinster, R. L., Nature, 296, 3942, 1982) or a heat shock promoter (Voellmy et al., Proc. Natl. Acad. Sci. USA, 82, 4949-53, 1985).

Bacterial, yeast, fungal, insect and mammalian cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in US NTIS Publication Ser. No. 08/043,109 (Hoffman, S., and Rogers, W.: Public. Date 1 Dec. 1993).

Thus, a still even more preferred form of this embodiment of the invention relates to Live Recombinant Carrier microorganisms (LRCs) comprising a gene encoding the UreX or UreY polypeptide or an immunogenic fragment thereof according to the invention. Such microorganisms are e.g. bacteria and viruses. These LRC microorganisms are microorganisms in which additional genetic information, in this case a gene encoding the UreX or UreY polypeptide or an immunogenic fragment thereof according to the invention has been cloned. Animals infected with such LRCs will produce an immunogenic response not only against the immunogens of the vector, but also against the immunogenic parts of the polypeptide(s) for which the genetic code is additionally cloned into the LRC, e.g. the ureX or Y gene.

As an example of bacterial LRCs, attenuated *Salmonella* strains known in the art can attractively be used.

Live recombinant carrier parasites have i.a. been described by Vermeulen, A. N. (Int. Journ. Parasitol. 28: 1121-1130 (1998)).

Also, LRC viruses may be used as a way of transporting the nucleic acid sequence into a target cell. Live recombinant carrier viruses are also called vector viruses. The site of integration of the gene encoding a UreX or Y polypeptide may be a site in a viral gene that is not essential to the virus, or a site in an intergenic region. Viruses often used as vectors are Vaccinia viruses (Panicali et al; Proc. Natl. Acad. Sci. USA, 79: 4927 (1982), Herpesviruses (E.P.A. 047321 OA2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic acid sequence into the genome of a bacterium, parasite or virus of choice, capable of inducing expression of the inserted nucleic acid sequence according to the invention in the host animal.

Finally, another form of this embodiment of the invention relates to a host cell comprising a nucleic acid sequence encoding a polypeptide according to the invention, a DNA fragment comprising such a nucleic acid sequence or a recombinant DNA molecule comprising such a nucleic acid sequence under the control of a functionally linked promotor. This form also relates to a host cell containing a live recombinant carrier containing a nucleic acid molecule encoding a UreX or Y polypeptide or an immunogenic fragment thereof according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the polypeptides encoded by the nucleic acid sequences, i.e. the urease X subunit and the urease Y subunit and to immunogenic fragments thereof according to the invention.

Therefore, this embodiment of the invention relates to the *Helicobacter felis* urease X polypeptide, said polypeptide having an amino acid sequence that is at least 85% homologous to SEQ ID NO: 2, or an immunogenic fragment of that polypeptide with a length of at least 40 amino acids that is capable of inducing an immune response against ureaseXY. Preferably, the length of that fragment is more than 40 amino acids, more preferably at least 45, 50, 55, 60 or 70 amino acids in that order or preference.

Preferably this embodiment relates to such polypeptides having a sequence homology of at least 90%, more preferably 94%, even more preferably 97% homology to SEQ ID NO: 2, or an immunogenic fragment of that polypeptide with a length of at least 40 amino acids, more preferably at least 45, 50, 55, 60 or 70 amino acids in that order or preference that is capable of inducing an immune response against ureaseXY.

This embodiment of the invention also relates to the *Helicobacter felis* urease Y polypeptide, said polypeptide having an amino acid sequence that is at least 85% homologous to SEQ ID NO: 3, or an immunogenic fragment of that polypeptide with a length of at least 40 amino acids that is capable of inducing an immune response against ureaseXY. Preferably, the length of that fragment is more than 40 amino acids, more preferably at least 45, 50, 55, 60 or 70 amino acids in that order or preference.

Preferably this embodiment relates to such polypeptides having a sequence homology of at least 90%, more preferably 94%, even more preferably 97% homology to SEQ ID NO: 3, or an immunogenic fragment of that polypeptide with a length of at least 40 amino acids, more preferably at least 45, 50, 55, 60 or 70 amino acids in that order or preference that is capable of inducing an immune response against ureaseXY.

As for the nucleotide sequence comparison, the comparison between the various amino acid sequences was made using Align Plus for Windows, available from Scientific and Educational Software, P.O. Box 72045 Durham, N.C. 27722-2045, USA. Settings used for the amino acid comparisons are indicated in FIGS. 1*a*, 1*b* and 1*c*.

It will be understood that, for the particular polypeptides embraced herein, natural variations can exist between individual *Helicobacter felis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, LeuNal and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting polypeptides retain their immunoreactivity. Thus, variations not essentially influencing the immunogenicity of the polypeptide compared to the wild type polypeptide as depicted in SEQ ID NO: 2 or 3 are considered to fall within the scope of the invention. Those variations in the amino acid sequence of a certain structural subunit X or Y according to the invention that still provide a polypeptide capable of inducing an immune response against infection with *H. felis* or at least against the clinical manifestations of the infection are considered as "not essentially influencing the immunogenicity".

When a polypeptide is used for e.g. vaccination purposes or for raising antibodies, it is however not necessary to use the whole polypeptide. It is also possible to use a fragment of that polypeptide that is capable, as such or coupled to a carrier such as e.g. KLH, of inducing an immune response against that polypeptide, a so-called immunogenic fragment. An "immunogenic fragment" is understood to be a fragment of the full-length polypeptide of the structural subunit X or Y that still has retained its capability to induce an immune response in the host, i.e. comprises a B- or T-cell epitope. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl Acad. Sci. 81: 3998-4002 (1984), J. Imm. Meth. 102, 259-274 (1987), the so-called PEPSCAN method is an easy to perform, quick and well-established method for the detection of epitopes, the immunologically important regions of the polypeptide. The method is used world-wide and as such well-known to persons skilled in the art. This (empirical) method is especially suitable for the detection of B-cell epitopes. Also, given the sequence of the gene encoding any protein, computer algorithms are able to designate specific polypeptide fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application NTIS U.S. Ser. No. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HIV-epitopes; The FASEB Journal 5:2412-2418 (1991).

Vaccines against e.g. *Helicobacter pylori*, which has only one urease, can be made on the basis of this urease, as was described above. In the specific case of *Helicobacter felis*, however, a vaccine based upon the known *Helicobacter felis* structural subunits ureA and B is not capable of providing sufficient protection against *Helicobacter felis* infection: immunity against structural subunits ureA and B allegedly does not neutralise the urease activity of the newly found heterologous structural subunits UreX and Y.

Therefore, vaccines for the protection of animals against *Helicobacter felis* infection should at least be directed against the novel urease XY. Therefore, one form of still another embodiment of the invention relates to vaccines capable of protecting mammals such as dogs and cats against *Helicobacter felis* infection, that comprise the structural subunit X or Y, preferably X and Y, more preferably X, Y, A and B, or an immunogenic fragment of X and/or Y according to the invention together with a pharmaceutically acceptable carrier.

Still another embodiment of the present invention relates to the polypeptides according to the invention for use in a vaccine.

Still another embodiment relates to the use of the polypeptide according to the invention in the manufacturing of a vaccine for combating *Helicobacter felis* infections.

One way of making a vaccine according to the invention is by biochemical purification of the ureaseXY polypeptide or its subunits from a bacterial culture. This can e.g. be done by centrifugation of the bacteria, and the use of gel-filtration columns for separation of the urease polypeptide or its subunits from other components. Further purification may e.g. be done by selective precipitation in ammonium-sulphate, followed by centrifugation, gel electrophoresis and, if desired, separation from the urease AB subunits and dissolving the pellet in a suitable buffer. This is, however, a time-consuming way of making the vaccine, especially where *Helicobacter felis* is difficult to grow.

It is therefore much more convenient to use the expression products of the genes encoding the urease X and Y subunits according to the invention in vaccines. Such vaccines can easily be made by admixing ureaseXY or a UreX or Y subunit or a immunological fragment thereof according to the invention with a pharmaceutically acceptable carrier as described below.

Furthermore, vaccines can comprise live recombinant carriers as described above, capable of expressing ureaseXY, a UreX or UreY subunit or immunogenic fragments thereof according to the invention. Such vaccines, e.g. based upon a *Salmonella* carrier or a viral carrier infecting the gastric epithelium have the advantage over subunit vaccines that they better mimic the natural way of infection of *Helicobacter felis*. Moreover, their self-propagation is an advantage since only low amounts of the recombinant carrier are necessary for immunization.

Vaccines described above all contribute to active vaccination, i.e. the host's immune system is triggered by the UreX and/or Y polypeptide or immunogenic fragments thereof, to make antibodies against these polypeptides.

Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Helicobacter* UreX or UreY can in these cases bind directly to the urease excreted by the bacteria. This has the advantage that the urease activity is directly eliminated, thus resulting in acidification of the environment and decreased or stopped *Helicobacter* growth.

Therefore, one other form of this embodiment of the invention relates to vaccines comprising antibodies against *Helicobacter felis* urease X polypeptides that have an amino acid sequence that is at least 85% homologous to SEQ ID NO: 2 or immunogenic fragments of that polypeptide with a length of at least 40 amino acids that are capable of inducing an immune response against ureaseXY or antibodies against *Helicobacter* fells urease Y polypeptides that have an amino acid sequence that is at least 85% homologous to SEQ ID NO: 3 or immunogenic fragments of that polypeptide with a length of at least 40 amino acids that are capable of inducing an immune response against ureaseXY.

Vaccines can also be based upon host cells as described above, that comprise ureaseXY, a UreX or UreY subunit or immunogenic fragments thereof according to the invention.

An alternative and efficient way of vaccination is direct vaccination with DNA encoding the relevant antigen. Direct vaccination with DNA encoding polypeptides has been successful for many different polypeptides. (As reviewed in e.g. Donnelly et al., The Immunologist 2: 20-26 (1993)). This way of vaccination is very attractive for the vaccination of both cats and dogs against *Helicobacter felis* infection.

Therefore, still other forms of this embodiment of the invention relate to vaccines comprising nucleic acid sequences encoding a polypeptide according to the invention or immunogenic fragments thereof according to the invention, and to vaccines comprising DNA fragments that comprise such nucleic acid sequences.

Still other forms of this embodiment relate to vaccines comprising recombinant DNA molecules according to the invention.

DNA vaccines can easily be administered through intradermal application e.g. using a needleless injector. This way of administration delivers the DNA directly into the cells of the animal to be vaccinated. An amount of DNA in the microgram range between 1 and 100 μg provides very good results.

In a further embodiment, the vaccine according to the present invention also comprises antigens from other dog or cat pathogenic organisms and viruses, or genetic information encoding such antigens. Such organisms and viruses are e.g. Feline Infectious Peritonitis virus, Feline Immune deficiency virus, Canine and Feline Parvovirus, Distemper virus, Adenovirus, Calicivirus, *Bordetella bronchiseptica, Borrelia burgdorferi, Leptospira interrogans, Chlamydia* and *Bartonella henseli.*

Also, the present invention relates to polypeptides according to the invention for use in the manufacturing of a vaccine for combating *Helicobacter felis* infections.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Vaccines according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyidipeptides, Quill A®, mineral oil e.g. Bayol® or Markol®, vegetable oil, and Carbopol® (a homopolymer), or Diluvac® Forte.

The vaccine may also comprise a so-called "vehicle". A vehicle is a compound to which the polypeptide adheres, without being covalently bound to it. Often used vehicle compounds are e.g. aluminium hydroxide,—phosphate or—oxide, silica, Kaolin, and Bentonite. A special form of such a vehicle, in which the antigen is partially embedded in the vehicle, is the so-called ISCOM (EP 109.942, EP 180.564, EP 242.380).

In addition, the vaccine may comprise one or more suitable surface-active compounds or emulsifiers, e.g. Span or Tween.

Often, the vaccine is mixed with stabilisers, e.g. to protect degradation-prone polypeptides from being degraded, to enhance the shelf-life of the vaccine, or to improve freeze-drying efficiency. Useful stabilizers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent. It goes without saying that other ways of adjuvating, adding vehicle compounds or diluents, emulsifying or stabilizing a polypeptide are also embodied in the present invention.

Vaccines according to the invention that comprise the UreX or UreY subunit polypeptide can very suitably be administered in amounts ranging between 1 and 100 micrograms, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for, respectively, bacteria and viruses.

Many ways of administration can be applied. Intranasal application is a frequently used way of administering a vaccine. Oral application is also an attractive way of administration, because the infection is often located in the upper digestive tract. A preferred way of oral administration is the packaging of the vaccine in capsules, known and frequently used in the art, that only disintegrate in the highly acidic environment of the stomach. Also, the vaccine could be mixed with compounds known in the art for temporarily enhancing the pH of the stomach. Systemic application is also suitable, e.g. by intramuscular application of the vaccine. If this route is followed, standard procedures known in the art for systemic application are well-suited.

Another embodiment of the invention relates to diagnostic tests for the detection of *H. felis* infection. It is known that several *Helicobacter* species such as *H. bizzozeronii, H. felis* and *H. salomonis* are capable of infecting both cats and dogs. Of these three, *H. felis* is the species suspected to cause most of the pathology, although it is often outnumbered by *H. bizzozeronii* and *H. salomonis*. Thus, a quick and correct diagnosis of disease, in both cats and dogs, caused by *Helicobacter felis* important. It has however been very difficult to discriminate between these three species due to the fact that they are so very closely related. Therefore, it is another objective of this invention to provide such diagnostic tools suitable for discriminating *H. felis* from other *Helicobacter* species.

On the basis of the novel urease polypeptides and the genes encoding the urease polypeptides, at least three different diagnostic tests, specifically suitable for the discrimination of *H. felis* from other members of the *Helicobacter* family were developed:

1) a diagnostic test based upon the presence or absence of DNA encoding the specific UreX and UreY structural subunits 2) a diagnostic test based upon the detection of antibodies against the specific UreX and UreY structural subunits 3) a diagnostic test based upon the detection of antigenic material of the specific UreX and UreY structural subunits A diagnostic test according to 1) is e.g. based upon the reaction of bacterial DNA isolated from the animal to be tested, with specific probes or PCR primers based upon the sequence of ureX or Y genes. If *H. felis* DNA is present in the animal, this will e.g. specifically bind to ureX or Y specific PCR primers and will subsequently become amplified in a PCR reaction. The PCR reaction product can then easily be detected in DNA gel electrophoresis.

The DNA can most easily be isolated from the microorganisms present in swabs of the upper digestive tract or in the saliva of the animal to be tested. Specific primers can easily be selected from the many regions of the ureX and ureY coding sequences and the non-coding intergenic sequence that differs in sequence from the comparable regions in the ureAB coding sequences. One of the many algorithms suitable for the determination of the level of nucleic acid homology and for comparison of nucleotide sequences in general is known as "Clustal W". It has been described by Thompson et al., in Nucleic Acid Research 22: 4673-4680 (1994). The program can be found at several sites on Internet. A more recent alternative for this program is e.g. Align Plus for Windows, available from Scientific and Educational Software, P.O. Box 72045 Durham, N.C. 27722-2045, USA.

As follows from FIG. 1, a large number of possible PCR primers can be found that are specific for ureX or urey. An extremely specific pair of PCR probes is e.g. formed by the 5'-located sequence CATGCACTTTTTGAAAAAAGA (SEQ ID NO: 16) and the 3'-located sequence TATGGTG-GTCTTCTCT (SEQ ID NO: 17). Of course, many other sequences that are specific for ureX or Y or the intergenic region are suitable. Standard PCR textbooks give methods for determining the suitability of the probes for selective PCR reactions with ureX or urey. PCR techniques are extensively described in (Dieffenbach & Dreksler; PCR primers, a laboratory manual. ISBN 0-87969447-5 (1995)).

Another DNA-based test is based upon growth of bacterial material obtained from the swab, followed by classical DNA purification followed by classical hybridization with radioactively or color-labelled ureXY-specific DNA-fragments. Given the very low homology between the ureXY-coding regions and the ureAB coding regions of both *H. felis* and other *Helicobacter* species, hybridization unambiguously indicates the presence or absence of *H. felis*. Both PCR reactions and hybridization reactions are well-known in the art and are i.a. described in Maniatis/Sambrook (Sambrook, J. et al. Molecular cloning: a laboratory manual. ISBN 0-87969-309-6).

Selective detection with PCR primers or with classical hybridization with ureXY-specific DNA-fragments can be done with fragments that preferably are short, but for practical reasons preferably consist of a stretch of at least 10 contiguous nucleotides of SEQ ID NO: 1. It is clear that for hybridization experiments a probe needs to be selected that has a higher homology to SEQ ID NO: 1, than to sequences encoding the *Helicobacter* ureA or ureB subunit. Such a probe can very easily be selected with the help of the Align Plus for Windows program or the Clustal W program as discussed above. In a comparative hybridization experiment the DNA to be diagnosed can be tested next to e.g. *H. pylori* DNA. The probe according to the invention, having a higher homology to SEQ ID NO: 1 than to a gene encoding ureAB, would bind better to *H. felis* DNA (if present in the sample) than to DNA of other *Helicobacter* species, thus specifically revealing the presence of *H. felis* DNA in the sample to be tested. The sequences SEQ ID NO: 16 or 17 mentioned above are merely examples of probes very suitable for labelling and subsequent use in the *H. felis*-specific hybridization assays as described.

Thus, one embodiment of the invention relates to a diagnostic test for the detection of DNA encoding the specific *Helicobacter* UreX and UreY subunit polypeptides. Such a test comprises a nucleic acid sequence according to the invention or a fragment thereof that is specific for the DNA encoding UreX and UreY or the intergenic region between UreX and UreY. A fragment that is specific for that DNA is a fragment that binds better to the DNA encoding UreX and UreY or the intergenic region between UreX and UreY than to the DNA encoding UreA and UreB or the intergenic region between UreA and UreB.

Methods for the detection of *Helicobacter felis* DNA comprise hybridization of the DNA to be tested with UreX or Y DNA, or PCR reaction of the DNA to be tested with UreX or Y DNA specific probes.

A diagnostic test according to 2) for the detection of *Helicobacter felis* antibodies in sera can be e.g. a simple sandwich-ELISA-test in which purified UreX or UreY subunit polypeptides or antigenic fragments thereof according to the invention are coated to the wall of the wells of an ELISA plate. A method for the detection of such antibodies is e.g. incubation of purified UreX or Y polypeptide with serum from mammals to be tested, followed by e.g. incubation with a labelled antibody against the relevant mammalian antibody.

A color reaction can then reveal the presence or absence of antibodies against *Helicobacter felis* urease XY. Depending on the labelled antibodies used, the selectivity of this system can be improved by pre-incubation of the serum to be tested with urease AB followed by spinning down the precipitate, in order to avoid non-XY-specific reactions.

If antigenic fragments of the UreX or UreY structural subunits according to the invention are used for coating, this pre-incubation step can be skipped.

Another example of a diagnostic test system is e.g. the incubation of a Western blot comprising UreX or UreY polypeptide, or an antigenic fragment thereof according to the invention, with serum of mammals to be tested, followed by analysis of the blot. The purified UreX and UreY structural subunits or antigenic fragments thereof according to the invention, suitable for the coating of ELISA plates or for Western blotting can easily be obtained by expression of the ureX and ureY gene as was described by Ferrero for ureA and B (Ferrero et al., Molec. Microbiol. 9, 323-333 (1993)).

Also, the invention relates to methods for the detection in serum of antibodies against *Helicobacter felis* antibodies, in which the method comprises the incubation of serum with UreX or UreY polypeptide or an antigenic fragment thereof according to the invention.

A diagnostic test according to 3) based upon the detection of antigenic material of the specific UreX and UreY structural subunits of *Helicobacter felis* antigens and therefore suitable for the detection of *Helicobacter felis* infection can e.g. also be a standard ELISA test. In one example of such a test the walls of the wells of an ELISA plate are coated with antibodies directed against the specific UreX and UreY structural subunits of *Helicobacter felis*. The antigenic material to be tested can if necessary be pre-incubated with antibodies against UreA and B. This will leave the UreX and Y specific epitopes uncovered and, therefore, the pre-incubated *Helicobacter* species will bind to the ELISA plate only if it comprises UreX or Y, i.e. if it specifically is *Helicobacter felis*. The use of monoclonal antibodies specific for UreX or Y, and not reacting with UreA or B, are the preferred antibodies in such tests, because they make the pre-incubation step superfluous. Such monoclonal antibodies can easily be obtained by immunizing inbred mice with immunizing fragments of UreX or Y according to the invention, by techniques also known in the art (See below: Kohler and Milstein).

The polypeptides or immunogenic fragments thereof according to the invention expressed as characterised above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the polypeptide according to the invention (or variants or fragments thereof) according to the present invention, can be prepared by immunizing inbred mice by techniques also known in the art (Kohler and Milstein, *Nature*, 256, 495-497, 1975).

Finally, the invention relates to methods for the detection of antigenic material from *Helicobacter felis* in which the method comprises the incubation of serum, tissue or body fluids with antibodies against UreX or UreY polypeptide or an antigenic fragment thereof according to the invention.

EXAMPLE 1

The ureX and ureY genes of *Helicobacter felis* strain CS1: cloning and expression in *Escherichia coli*.

The ureX and ureY genes of *H. felis* strain CS1 were cloned as an operon into an *E. coli* T7 expression vector, pET3a, as follows:

For proper expression of the UreX and Y proteins in pET3a (Novagen, 601 Science Drive, Madison Wis., USA), the genes were cloned as a NdeI-BamHI DNA fragment into the NdeI-BamHI sites of this vector. The ureaseXY operon contains an internal NdeI site that was mutated by overlap-extension PCR of 2 PCR fragments. For that purpose two PCR fragments (the 5' and the 3' products) were amplified using chromosomal DNA of *H. felis* CS1 as the template. The 5' PCR product contained the complete ureX gene and the first part of the ureY gene. The forward primer contained a NdeI restriction site and the start codon of ureX (GGAGTAA-CATATGAAACTCACA CCCAAAGAGC) (SEQ ID NO: 18), and the reverse primer contains a point mutation (CA-CACCCACGACCATGTGAGGGCTTAC) (SEQ ID NO: 19). The second 3' PCR product consisted of the 3' end of the ureY gene. This forward primer is complementary to the reverse primer of the first PCR product and also contained the same point mutation (GTAAGCC CTCACATG-GTCGTGGGTGTG) (SEQ ID NO: 20) and the reverse primer contained a BamHI restriction site just downstream of the stopcodon of the ureY gene (CGAATTCGGATCCTA-GAAGAAAGTGTAGCGCTGG)(SEQ ID NO: 21). The mutation in the complementary primers is made to delete the internal NdeI site in urey, in which it replaces the CA<u>T</u>ATG (His- Met) by CA<u>C</u>ATG (His-Met).

After amplification of both PCR products, the complete operon was obtained by overlap-extension-PCR with the forward primer of the ureX and the reverse primer of the ureY using both PCR products as templates. The resulting PCR product was cloned into PCR-bluntII-TOPO (Invitrogen, P.O. Box 2312, 9704 CH Groningen, The Netherlands) and transformed into *E. coli* TOP10F' cells (Invitrogen). Positive clones were isolated and the ureaseXY genes were subcloned into pET3a with NdeI-BamHI. The obtained plasmid was called pUreXY-1 and was transformed into the expression strain HMS174(DE3)/pLysS (Novagen).

The ureX and ureY genes of pUreXY-1 were expressed in HMS174(DE3)/pLysS as follows: an overnight culture was diluted 1/100 into TB Amp$^{100}$ Cam$^{25}$; this culture was incubated for 3 h at 37° C. at 200 rpm; the culture was induced by adding 1 mM of IPTG and incubated for another 3 h at 37° C. at 200 rpm. The induction was done twice, once in a small scale and once in a large scale. The induced samples were analysed on a SDS-PAGE gel (FIG. 2). As can be clearly seen from lane 9, expression of UreX and UreY, when induced provides the two structural subunits as polypeptide bands with a molecular weight of 25 kDa for the UreX subunit and 62 kDa for the UreY subunit.

The invention claimed is:

1. An isolated nucleic acid molecule consisting of nucleotides 206-2603 of SEQ ID NO: 1 and variants thereof that are at least 94% identical over the entire length of nucleotides 206-2603 of SEQ ID NO: 1; wherein said nucleic acid molecule encodes a urease protein having enzymatic activity that catalyzes the hydrolysis of urea.

2. A recombinant DNA molecule comprising the isolated nucleic acid molecule of claim 1 or said variants thereof, wherein said isolated nucleic acid molecule or said variants thereof are under the control of a functionally linked promoter.

3. A live recombinant carrier comprising the recombinant DNA molecule of claim 2.

4. An isolated host cell comprising the nucleic acid molecule of claim 1 or said variants thereof.

5. An isolated host cell comprising the recombinant DNA molecule of claim 2.

6. An isolated host cell comprising the live recombinant carrier of claim 3.

7. The isolated nucleic acid molecule of claim 1, wherein said nucleic acid molecule is nucleotides 206-2603 of SEQ ID NO: 1.

* * * * *